United States Patent
Gurevich et al.

(10) Patent No.: US 11,660,057 B2
(45) Date of Patent: May 30, 2023

(54) SYSTEMS AND METHODS FOR PERSISTENT URETER VISUALIZATION

(71) Applicant: Stryker Corporation, Kalamazoo, MI (US)

(72) Inventors: Lina Gurevich, Vancouver (CA); Arthur E. Bailey, North Vancouver (CA)

(73) Assignee: Stryker Corporation, Kalamazoo, MI (US)

( * ) Notice: Subject to any disclaimer, the term of this patent is extended or adjusted under 35 U.S.C. 154(b) by 64 days.

(21) Appl. No.: 16/925,645

(22) Filed: Jul. 10, 2020

(65) Prior Publication Data

US 2021/0007687 A1 Jan. 14, 2021

Related U.S. Application Data

(60) Provisional application No. 62/872,517, filed on Jul. 10, 2019.

(51) Int. Cl.
*A61B 6/00* (2006.01)
*A61B 90/00* (2016.01)
*G06T 7/00* (2017.01)

(52) U.S. Cl.
CPC ............ *A61B 6/4417* (2013.01); *A61B 6/461* (2013.01); *A61B 6/481* (2013.01); *A61B 6/485* (2013.01);
(Continued)

(58) Field of Classification Search
CPC ......... G06T 7/0012; G06T 2207/10064; G06T 2207/20081; G06T 2207/20084;
(Continued)

(56) References Cited

U.S. PATENT DOCUMENTS

| | | | | |
|---|---|---|---|---|
| 2014/0028824 | A1* | 1/2014 | Kubo | A61B 1/043 348/77 |
| 2016/0353968 | A1* | 12/2016 | Ikuma | A61B 1/00 |

(Continued)

OTHER PUBLICATIONS

Hockenberry e al. "A novel use of near-infrared fluorescence imaging during robotic surgery without contrast agents." Journal of Endourology 28.5 (2014): 509-512. (Year: 2014).*

(Continued)

*Primary Examiner* — Katrina R Fujita
(74) *Attorney, Agent, or Firm* — Morrison & Foerster LLP

(57) ABSTRACT

A method for visualizing tissue of a subject includes receiving a first series of first imaging modality frames generated by imaging a region of tissue of the subject, and a first series of second imaging modality frames generated by imaging the region of tissue; displaying the first series of first imaging modality frames in combination with the first series of second imaging modality frames; storing a plurality of first imaging modality frames and a plurality of second imaging modality frames of the first series of second imaging modality frames in a memory; receiving a second series of first imaging modality frames generated by imaging the region of tissue; and displaying the second series of first imaging modality frames in combination with one or more of the second imaging modality frames of the first series of second imaging modality frames stored in the memory for visualizing the region of tissue.

37 Claims, 12 Drawing Sheets
(1 of 12 Drawing Sheet(s) Filed in Color)

(52) U.S. Cl.
CPC ............ *A61B 90/37* (2016.02); *G06T 7/0012* (2013.01); *A61B 2090/376* (2016.02); *G06T 2207/10064* (2013.01); *G06T 2207/20081* (2013.01); *G06T 2207/20084* (2013.01); *G06T 2207/30004* (2013.01)

(58) Field of Classification Search
CPC ........ G06T 2207/30004; A61B 6/4417; A61B 6/461; A61B 6/481; A61B 6/485; A61B 90/37; A61B 2090/376
See application file for complete search history.

(56) References Cited

U.S. PATENT DOCUMENTS

| | | | |
|---|---|---|---|
| 2017/0038951 A1* | 2/2017 | Reicher | G06F 16/583 |
| 2017/0181701 A1* | 6/2017 | Fehrenbacher | A61B 17/29 |
| 2019/0128989 A1 | 5/2019 | Braun et al. | |
| 2019/0247126 A1* | 8/2019 | Ikehara | A61B 5/14556 |
| 2020/0237452 A1* | 7/2020 | Wolf | G06F 3/048 |
| 2020/0273575 A1* | 8/2020 | Wolf | A61B 34/70 |

OTHER PUBLICATIONS

Mahalingam et al. "Intraoperative ureter visualization using a novel near-infrared fluorescent dye." Molecular pharmaceutics 15.8 (2018): 3442-3447. (Year: 2018).*

Yu et al. "An augmented reality endoscope system for ureter position detection." Journal of Medical Systems 42.8 (2018): 1-12. (Year: 2018).*

Yu et al. "Laparoscopic image-guided system based on multispectral imaging for the ureter detection." IEEE Access 7 (2018): 3800-3809. (Year: 2018).*

International Preliminary Report on Patentability dated Jan. 11, 2022, directed to International Application No. PCT/CA2020/050957; 7 pages.

International Search Report and Written Opinion dated Aug. 25, 2020, directed to International Application No. PCT/CA2020/050957; 11 pages.

Matsui et al., (Jul. 2010) "Real-Time Near-Infrared Fluorescence-Guided Identification of the Ureters using Methylene Blue," Surgery 148(1): 78-76.

Nagaya et al., (Dec. 22, 2017). "Fluorescence-Guided Surgery," Frontiers in Oncology 7(314):1-16.

* cited by examiner

SYSTEMS AND METHODS FOR PERSISTENT URETER VISUALIZATION

CROSS-REFERENCE TO RELATED APPLICATIONS

This application claims the benefit of U.S. Provisional Application No. 62/872,517, filed Jul. 10, 2019, the entire contents of which are hereby incorporated by reference herein.

FIELD OF THE INVENTION

The present disclosure relates generally to medical imaging, and more particularly to acquiring and processing medical images for visualizing tissue of a subject.

BACKGROUND OF THE INVENTION

Laparoscopic procedures are minimally invasive surgical procedures in the abdominal and pelvic areas. Abdominal and pelvic surgeries pose a risk of accidental injury to the tissues of the renal system, particularly the ureters. Ureters are small-diameter vessels that carry urine from the kidneys to the bladder. Ureters may be difficult to identify in a surgical field due to their small diameter and because they are often covered by other tissue. This is especially true in laparoscopic procedures because the surgeon has a limited view of the surgical field and cannot use tactile perception to aid in identification of the ureters. Thus, in laparoscopic procedures there is often a risk that the ureters may be unintentionally injured. Further, such injuries are often not detected during the surgical procedure and detection may be delayed for days or months.

To help avoid injury, intravenous pyelography, retrograde pyelography, or urological computed tomography can be performed preoperatively to locate the ureters. However, these imaging techniques do not provide real-time guidance during the actual surgical procedure. One method for visualizing a ureter during laparoscopic surgery includes inserting a lighted catheter or stent through the urethra and bladder and into the ureter. However, placement of a lighted ureteral catheter or stent is a highly invasive procedure that is associated with its own complications.

Fluorescence imaging has been used to visualize ureters intraoperatively. A fluorescence imaging agent that is excreted in the urine, such as methylene blue, is administered to the patient resulting in agent-containing urine moving through the ureters. A fluorescence imaging system captures the fluorescence emission of the agent as it moves through the ureter and generates fluorescence images of the ureters. However, due to the peristaltic nature of urine passage through the ureters, the imaging agent is only intermittently present in the ureters, and therefore, the ureters cannot be imaged continuously by the fluorescence imaging system.

SUMMARY OF THE INVENTION

According to some embodiments, systems and methods enable persistent visualization of a feature of tissue of a subject using an imaging modality that can only intermittently image the feature. Two imaging modalities are used to image the tissue of the subject. A first imaging modality continuously images the tissue and a second imaging modality periodically images a feature of the tissue. During periods when the second imaging modality is imaging the feature, the first and second imaging modality image frames are displayed together and stored together in memory. During periods when the second imaging modality is not imaging the feature, but the first imaging modality continues to image the tissue, second imaging modality frames are retrieved from the memory and displayed together with newly acquired first imaging modality frames. Thus, the feature of the tissue can be persistently displayed to the user.

Stored first imaging modality frames may be used to determine which second imaging modality frames to retrieve from the memory for display. During periods when the second imaging modality is not imaging the feature of the tissue, a newly acquired first imaging modality frame is compared to stored first imaging modality frames to identify a stored first imaging modality frame that is similar to the newly acquired frame. Once a similar stored first imaging modality frame is identified, the stored second imaging modality frame that corresponds to the identified first imaging modality frame is retrieved from the memory and displayed together with the newly acquired first imaging modality frame. Because of the similarity between the newly acquired first imaging modality frame and the similar first imaging modality frame stored in the memory, the second imaging modality frame should approximate the appearance of the feature of the tissue had it been imaged contemporaneously with the newly acquired first imaging modality frame.

According to some embodiments, a method for visualizing tissue of a subject includes receiving a first series of first imaging modality frames generated by imaging a region of tissue of the subject according to a first imaging modality, and a first series of second imaging modality frames generated by imaging the region of tissue of the subject according to a second imaging modality; displaying the first series of first imaging modality frames in combination with the first series of second imaging modality frames; storing a plurality of first imaging modality frames of the first series of first image modality frames and a plurality of second imaging modality frames of the first series of second imaging modality frames in a memory; receiving a second series of first imaging modality frames generated by imaging the region of tissue of the subject according to the first imaging modality; and displaying the second series of first imaging modality frames in combination with one or more second imaging modality frames that are associated with the first series of second imaging modality frames for visualizing the region of tissue of the subject.

In any of these embodiments, the method may further include selecting a frame of the plurality of second imaging modality frames stored in the memory for display in combination with a frame of the second series of first imaging modality frames based on a similarity between the frame of the second series of first imaging modality frames and a frame of the plurality of first imaging modality frames stored in the memory that is associated with the frame of the plurality of second imaging modality frames stored in the memory.

In any of these embodiments, selecting the frame of the plurality of second imaging modality frames may include calculating a similarity score for the frame of the second series of first imaging modality frames and the frame of the plurality of first imaging modality frames stored in the memory.

In any of these embodiments, selecting the frame of the plurality of second imaging modality frames may include determining that the similarity score is above a predetermined threshold.

In any of these embodiments, selecting the frame of the plurality of second imaging modality frames may include determining that the similarity score is greater than similarity scores for other frame of the plurality of first imaging modality frames stored in the memory.

In any of these embodiments, an attribute of a display of the selected frame of the plurality of second imaging modality frames stored in the memory in combination with the frame of the second series of first imaging modality frames may be based on the similarity score.

In any of these embodiments, the attribute may include at least one of increasing an area of fluorescence and altering a color scheme based on the similarity score.

In any of these embodiments, the similarity score may be a structural similarity metric, a mutual information metric, or a combination thereof.

In any of these embodiments, the second imaging modality may be fluorescence imaging and the method may further include ceasing to store second imaging modality frames in the memory based on a level of fluorescence intensity dropping below a threshold.

In any of these embodiments, the method may further include, after ceasing to store second imaging modality frames in the memory, storing a second series of second imaging modality frames in the memory in response to an increase in a level of fluorescence intensity.

In any of these embodiments, the first series of second imaging modality frames may include an image of a tissue feature that is not visible in the first series of first imaging modality frames.

In any of these embodiments, the first imaging modality may include visible light imaging and second imaging modality may include fluorescence imaging.

In any of these embodiments, the second imaging modality may include fluorescence imaging and the method may further include: receiving a third series of first imaging modality frames and a second series of second imaging modality frames; and storing a first frame of the third series of first imaging modality frames in place of a first frame of the first series of first imaging modality frames in the memory based on a level of fluorescence intensity of a first frame of the second series of second imaging modality frames that is associated with the first frame of the third series of first imaging modality frames.

In any of these embodiments, the method may further include storing the first frame of the second series of second imaging modality frames in place of a first frame of the first series of second imaging modality frames in the memory.

In any of these embodiments, the second imaging modality may include imaging of an imaging agent and the method may further include administering the imaging agent to the subject so that the imaging agent enters the region of tissue of the subject.

In any of these embodiments, the imaging agent may be a fluorescence imaging agent and the tissue of the region of tissue of the subject may include a ureter.

In any of these embodiments, the region of tissue of the subject may include a ureter and the imaging agent may be excretable in urine.

In any of these embodiments, the imaging agent may include at least one of methylene blue, phenylxanthenes, phenothiazines, phenoselenazines, cyanines, indocyanines, squaraines, dipyrrolo pyrimidones, anthraquinones, tetracenes, quinolines, pyrazines, acridines, acridones, phenanthridines, azo dyes, rhodamines, phenoxazines, azulenes, azaazulenes, triphenyl methane dyes, indoles, benzoindoles, indocarbocyanines, benzoindocarbocyanines, derivatives having the general structure of 4,4-difluoro-4-bora-3a,4a-diaza-s-indacene, and conjugates thereof and derivatives thereof.

In any of these embodiments, the second imaging modality may include imaging an imaging agent and at least a portion of the imaging agent may be carried by urine transiting through a ureter.

In any of these embodiments, the method may further include illuminating the region of tissue of the subject with visible light and fluorescence excitation light.

In any of these embodiments, the first series of first imaging modality frames and the first series of second imaging modality frames may be generated using a single imaging sensor.

In any of these embodiments, the first series of first imaging modality frames and the first series of second imaging modality frames may be generated using multiple imaging sensors.

In any of these embodiments, the first series of first imaging modality frames may be white light frames.

In any of these embodiments, displaying the second series of first imaging modality frames in combination with one or more second imaging modality frames that are associated with of the first series of second imaging modality frames stored in the memory may include displaying an overlay image, side-by-side images, or a picture-in-picture image.

In any of these embodiments, the first series of first imaging modality frames may be generated synchronously with the first series of second imaging modality frames.

In any of these embodiments, the first series of first imaging modality frames may be generated simultaneously with the first series of second imaging modality frames.

In any of these embodiments, the first and second series of first imaging modality frames may be displayed during a surgical procedure on the subject.

In any of these embodiments, the surgical procedure may be an abdominal or pelvic surgical procedure.

In any of these embodiments, the abdominal or pelvic surgical procedure may include at least one of total or partial hysterectomy, oophorectomy, tubal ligation, surgical removal of ovarian cysts, anterior repair of the vaginal wall, caesarean section, repair of a pelvic prolapse, pelvic mass resection, removal of a fallopian tube, adnexectomy, removal of an ectopic pregnancy, vasectomy, prostatectomy, hernia repair surgery, colectomy, cholecystectomy, appendectomy, hepatobiliary surgery, splenectomy, distal or total pancreatectomy, the Whipple procedure, and abdominal or pelvic lymphadenectomy.

In any of these embodiments, the first and second series of first imaging modality frames may be displayed in real time.

In any of these embodiments, the first series of first imaging modality frames and the first series of second imaging modality frames may be received from an imager.

In any of these embodiments, the first series of first imaging modality frames and the first series of second imaging modality frames may be received from a memory.

In any of these embodiments, the method can further include generating the one or more second imaging modality frames that are associated with the first series of second imaging modality frames by processing at least a portion of the first series of first imaging modality frames by a trained learning machine.

In any of these embodiments, the trained learning machine can have been trained on imaging data not associated with the subject.

In any of these embodiments, the trained learning machine can be based on a conditional Generative Adversarial Network.

According to some embodiments, a system for visualizing tissue of a subject includes a display; one or more processors; memory; and one or more programs, wherein the one or more programs are stored in the memory and configured to be executed by the one or more processors, the one or more programs including instructions for: receiving a first series of first imaging modality frames generated by imaging a region of tissue of the subject according to a first imaging modality, and a first series of second imaging modality frames generated by imaging the region of tissue of the subject according to a second imaging modality; displaying the first series of first imaging modality frames in combination with the first series of second imaging modality frames on the display; storing a plurality of first imaging modality frames of the first series of first image modality frames and a plurality of second imaging modality frames of the first series of second imaging modality frames in the memory; receiving a second series of first imaging modality frames generated by imaging the region of tissue of the subject according to the first imaging modality; and displaying, on the display, the second series of first imaging modality frames in combination with one or more second imaging modality frames that are associated with the first series of second imaging modality frames for visualizing the region of tissue of the subject.

In any of these embodiments, the system may further include a light source for providing visible illumination light and fluorescence excitation light to the region of tissue of the subject.

In any of these embodiments, the system may further include an imager for generating the first series of first imaging modality frames and the first series of second imaging modality frames.

In any of these embodiments, the one or more programs may include further instructions for selecting a frame of the plurality of second imaging modality frames stored in the memory for display in combination with a frame of the second series of first imaging modality frames based on a similarity between the frame of the second series of first imaging modality frames and a frame of the plurality of first imaging modality frames stored in the memory that is associated with the frame of the plurality of second imaging modality frames stored in the memory.

In any of these embodiments, selecting the frame of the plurality of second imaging modality frames may include calculating a similarity score for the frame of the second series of first imaging modality frames and the frame of the plurality of first imaging modality frames stored in the memory.

In any of these embodiments, selecting the frame of the plurality of second imaging modality frames may include determining that the similarity score is above a predetermined threshold.

In any of these embodiments, selecting the frame of the plurality of second imaging modality frames may include determining that the similarity score is greater than similarity scores for other frame of the plurality of first imaging modality frames stored in the memory.

In any of these embodiments, an attribute of a display of the selected frame of the plurality of second imaging modality frames stored in the memory in combination with the frame of the second series of first imaging modality frames may be based on the similarity score.

In any of these embodiments, the attribute may include at least one of increasing an area of fluorescence and altering a color scheme based on the similarity score.

In any of these embodiments, the similarity score may be a structural similarity metric, a mutual information metric, or a combination thereof.

In any of these embodiments, the second imaging modality may be fluorescence imaging and the one or more programs may include further instructions for ceasing to store second imaging modality frames in the memory based on a level of fluorescence intensity dropping below a threshold.

In any of these embodiments, the one or more programs may include further instructions for, after ceasing to store second imaging modality frames in the memory, storing a second series of second imaging modality frames in the memory in response to an increase in a level of fluorescence intensity.

In any of these embodiments, the first series of second imaging modality frames may include an image of a tissue feature that is not visible in the first series of first imaging modality frames.

In any of these embodiments, the first imaging modality may include visible light imaging and second imaging modality may include fluorescence imaging.

In any of these embodiments, the second imaging modality may include fluorescence imaging and the one or more programs may include further instructions for: receiving a third series of first imaging modality frames and a second series of second imaging modality frames; and storing a first frame of the third series of first imaging modality frames in place of a first frame of the first series of first imaging modality frames in the memory based on a level of fluorescence intensity of a first frame of the second series of second imaging modality frames that is associated with the first frame of the third series of first imaging modality frames.

In any of these embodiments, the one or more programs may include further instructions for storing the first frame of the second series of second imaging modality frames in place of a first frame of the first series of second imaging modality frames in the memory.

In any of these embodiments, the second imaging modality may include imaging of an imaging agent and the one or more programs may include further instructions for administering the imaging agent to the subject so that the imaging agent enters the region of tissue of the subject.

In any of these embodiments, the imaging agent may be a fluorescence imaging agent and the tissue of the region of tissue of the subject may include a ureter.

In any of these embodiments, the region of tissue of the subject may include a ureter and the imaging agent may be excretable in urine.

In any of these embodiments, the imaging agent may include at least one of methylene blue, phenylxanthenes, phenothiazines, phenoselenazines, cyanines, indocyanines, squaraines, dipyrrolo pyrimidones, anthraquinones, tetracenes, quinolines, pyrazines, acridines, acridones, phenanthridines, azo dyes, rhodamines, phenoxazines, azulenes, azaazulenes, triphenyl methane dyes, indoles, benzoindoles, indocarbocyanines, benzoindocarbocyanines, derivatives having the general structure of 4,4-difluoro-4-bora-3a,4a-diaza-s-indacene, and conjugates thereof and derivatives thereof.

In any of these embodiments, the second imaging modality may include imaging an imaging agent and at least a portion of the imaging agent may be carried by urine transiting through a ureter.

In any of these embodiments, the one or more programs may include further instructions for illuminating the region of tissue of the subject with visible light and fluorescence excitation light.

In any of these embodiments, the first series of first imaging modality frames and the first series of second imaging modality frames may be generated using a single imaging sensor.

In any of these embodiments, the first series of first imaging modality frames and the first series of second imaging modality frames may be generated using multiple imaging sensors.

In any of these embodiments, the first series of first imaging modality frames may be white light frames.

In any of these embodiments, displaying the second series of first imaging modality frames in combination with one or more second imaging modality frames that are associated with the first series of second imaging modality frames may include displaying an overlay image, side-by-side images, or a picture-in-picture image.

In any of these embodiments, the first series of first imaging modality frames may be generated synchronously with the first series of second imaging modality frames.

In any of these embodiments, the first series of first imaging modality frames may be generated simultaneously with the first series of second imaging modality frames.

In any of these embodiments, the first and second series of first imaging modality frames may be displayed during a surgical procedure on the subject.

In any of these embodiments, the surgical procedure may be an abdominal or pelvic surgical procedure.

In any of these embodiments, the abdominal or pelvic surgical procedure may include at least one of total or partial hysterectomy, oophorectomy, tubal ligation, surgical removal of ovarian cysts, anterior repair of the vaginal wall, caesarean section, repair of a pelvic prolapse, pelvic mass resection, removal of a fallopian tube, adnexectomy, removal of an ectopic pregnancy, vasectomy, prostatectomy, hernia repair surgery, colectomy, cholecystectomy, appendectomy, hepatobiliary surgery, splenectomy, distal or total pancreatectomy, the Whipple procedure, and abdominal or pelvic lymphadenectomy.

In any of these embodiments, the first and second series of first imaging modality frames may be displayed in real time.

In any of these embodiments, the first series of first imaging modality frames and the first series of second imaging modality frames may be received from an imager.

In any of these embodiments, the first series of first imaging modality frames and the first series of second imaging modality frames may be received from a memory.

In any of these embodiments, the one or more programs can include further instructions for generating the one or more second imaging modality frames that are associated with the first series of second imaging modality frames by processing at least a portion of the first series of first imaging modality frames by a trained learning machine.

In any of these embodiments, the trained learning machine can have been trained on imaging data not associated with the subject.

In any of these embodiments, the trained learning machine can be based on a conditional Generative Adversarial Network.

According to some embodiments, a non-transitory computer readable storage medium stores one or more programs for execution by one or more processors of a system for visualizing tissue of a subject, and the one or more programs include instructions for performing any of the above methods.

According to some embodiments, a kit for imaging tissue includes a fluorescence imaging agent and any of the above systems.

According to some embodiments, a fluorescence imaging agent is configured for use in any of the above methods for imaging tissue.

In any of these embodiments, imaging tissue may include imaging tissue during a laparoscopic procedure.

According to some embodiments, any of the above methods are used for ureter imaging.

BRIEF DESCRIPTION OF THE DRAWINGS

The patent or application file contains at least one drawing executed in color. Copies of this patent or patent application publication with color drawings(s) will be provided by the Office upon request and payment of the necessary fee. Features will become apparent to those of ordinary skill in the art by describing in detail exemplary embodiments with reference to the attached drawings in which.

DETAILED DESCRIPTION OF EXEMPLARY EMBODIMENTS

Figure 1:
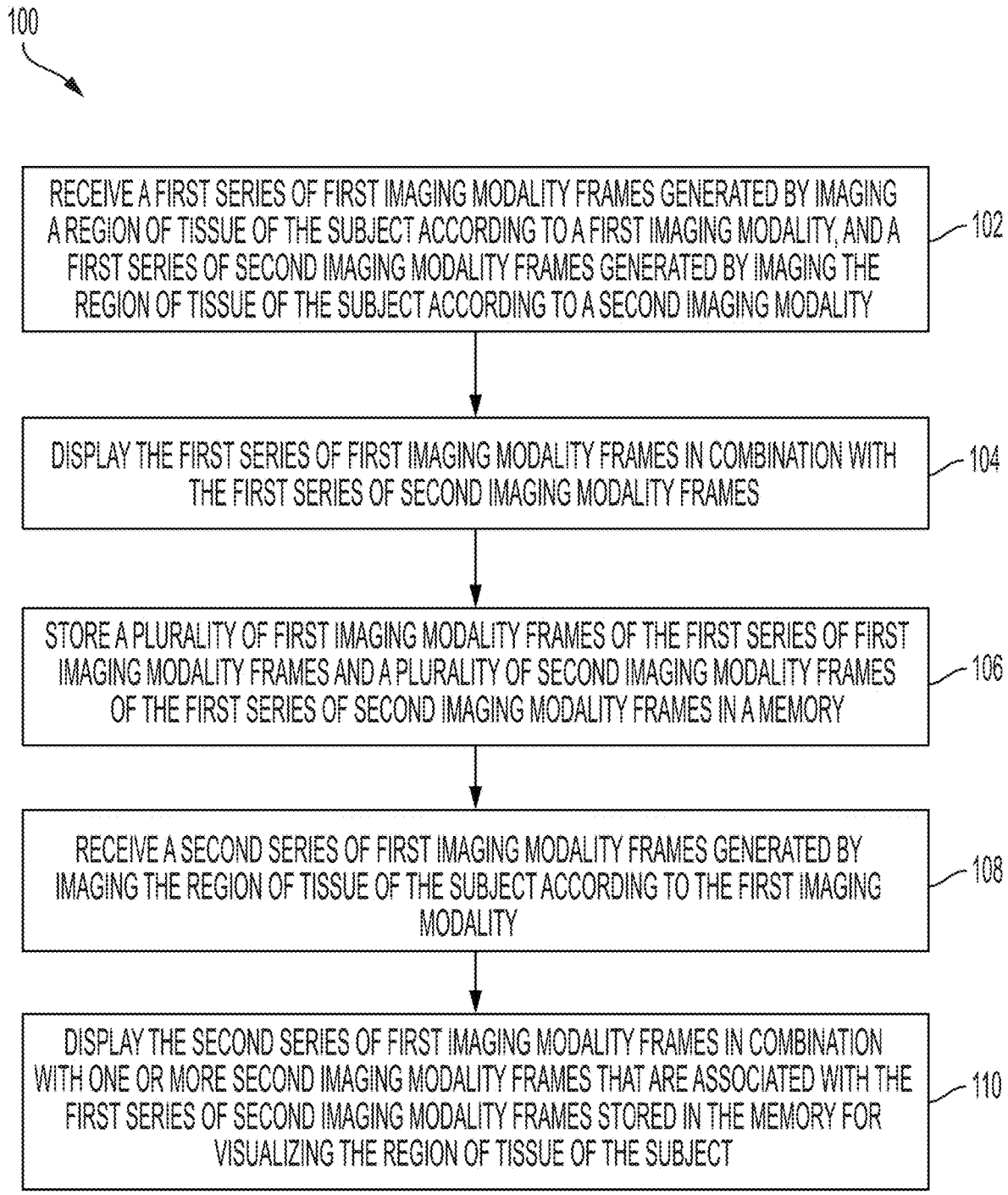
FIG. 1 illustrates a method for persistent visualization of a feature of tissue of a subject, according to some embodiments.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Described herein according to various embodiments are systems and methods for persistent visualization of a feature of interest of tissue of a subject despite only periodically imaging the feature of interest. According to some embodiments, two imaging modalities image the same region of tissue of the subject at the same time. The first imaging modality continuously images the tissue while the second imaging modality only periodically images the feature of interest. The periodic imaging of the feature of interest may be due to, for example, an imaging agent passing only periodically through the feature of interest and, thus, preventing the second imaging modality from imaging the feature during periods when the agent is absent from the feature of interest. During periods when the second imaging modality is able to image the feature of interest, first and second imaging modality images are displayed together for visualization by a user—for example, a fluorescence image can be displayed as an overlay on a white light image—and are stored together in memory. During periods when the second imaging modality is not imaging the feature and the first imaging modality continues to image the tissue, second imaging modality images are retrieved from the memory and displayed together with newly acquired first imaging modality images for visualization by the user. Thus, the feature of the tissue can be persistently visualized by the user.

Stored first imaging modality images are used to determine which second imaging modality images to retrieve from the memory for display. During periods when the second imaging modality is not imaging the feature of interest, a newly acquired first imaging modality image is compared to stored first imaging modality images to find a similar image. Once a first imaging modality image that is similar to the newly acquired image is found, its corresponding second imaging modality image—i.e., the second imaging modality image that was generated at the same or similar time—is retrieved from the memory and displayed together with the newly acquired first imaging modality image. Because of the similarity between the first imaging modality images (i.e., the newly acquired one and the similar stored one), the second imaging modality image should approximate the appearance of the feature of interest at the time that the newly acquired first imaging modality image was generated.

According to some embodiments, systems and methods for persistent visualization of a feature of interest of tissue of a subject can be used for persistent visualization of ureters, such as during laparoscopic surgery. Avoiding damage to ureters during surgery is important due to the difficulty in detecting the damage during the procedure and due to the complications that result from the damage. Ureters are difficult to avoid, however, because they are difficult for surgeons to visualize. This is for a number of reasons, including that the ureters are usually covered by other tissue, are long and thin, and are often in somewhat different locations from one person to the next. Fluorescence imaging has been used to aid surgeons in visualizing various types of tissue or features of tissue during surgical procedures. Ureters can be imaged by a fluorescence imaging system by utilizing fluorescence imaging agents that concentrate in urine. Imaging agents such as methylene blue enter urine via the kidneys and pass in the urine through the ureters and into the bladder. The passage of the agent through the ureters enables the imaging of the ureters by a fluorescence imaging system. Fluorescence images of the ureter can be displayed to a surgeon during the surgical procedure so that the surgeon can avoid the ureters.

However, passage of urine through the ureters is periodic due to uretral peristalsis, meaning that the fluorescence imaging agent will only periodically be present in the ureter. Thus, there will be periods of time during which fluorescence imaging will not be able to capture images of the ureter, which would result in loss of visualization of the ureter by the surgeon. However, systems and methods described herein can provide visualization of the ureter during these periods when the imaging agent is not present in the ureter (or the portion of the ureter that is within the imaging field of view) by displaying previously captured and stored fluorescence images of the ureter. According to various embodiments, this is done by using visible light images to find stored fluorescence images that correspond to the current scene. Each stored fluorescence image is stored together with a visible light image generated at the same or similar time. Stored visible light images are searched for an image that is similar to a newly generated visible light image. Upon finding a similar visible light image, the fluorescence image that corresponds to the similar visible light image is retrieved from memory and displayed to the user together with the newly acquired visible light image. Thus, to the user, it appears as if the ureter continues to be imaged.

According to various embodiments, although the scene in the field of view changes over time, due to, for example, the surgeon cutting away tissue, moving tissue around, moving tools with the field of view, or moving the camera, a particular scene may be repeated over the length of the procedure, such that stored images generated previously during the procedure may approximate a later scene. This may be particularly true in minimally invasive procedures in which the field of view is constrained to a relatively localized area. So, while there may be large variations in the imaged scene during the procedure, there may be a high likelihood that a given scene will be substantially repeated. Systems and methods, according to various embodiments, take advantage of this aspect of minimally invasive procedures and use previously stored images to persistently represent a feature of interest.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 illustrates a method 100 for persistent visualization of a feature of interest of tissue of a subject. Method 100 utilizes at least two imaging modalities—a first imaging modality that continuously images the tissue of the subject and a second imaging modality that periodically images the feature of interest of the tissue of the subject. Method 100 can be used to persistently display the feature of interest during periods when the second imaging modality is no longer imaging the feature. The second imaging modality may stop imaging the feature for any number of reasons, such as because the second imaging modality relies upon an imaging agent that is only periodically present in the tissue or because the second imaging modality is used only periodically rather than continuously, such as to reduce an amount of radiation exposure of the subject. During periods when the second imaging modality is not imaging the feature of interest, previously generated and stored images of the feature of interest can be used to persistently visualize the feature of interest.

At step 102, a first series of first imaging modality frames generated by imaging a region of tissue of the subject according to a first imaging modality are received along with a first series of second imaging modality frames generated by imaging the region of tissue of the subject according to a second imaging modality. The first and second series may be received from an imager or imaging system or may be received from a memory. The two imaging modalities may be capable of imaging different features or aspects of the tissue of the subject. The first imaging modality may image features of the tissue or aspects of the tissue that are not imaged by the second imaging modality, and vice versa. For example, the first imaging modality may be visible light imaging that produces images of visible light that reflects off of the surface of the tissue within the field of view, and the second imaging modality may include imaging an imaging agent such that portions of the tissue beneath the surface in the field of view can be imaged. Examples of imaging modalities include narrow band imaging, fluorescence imaging, x-ray imaging, and ultrasound imaging.

The first and second series of frames are time series of frames generated over a period of time. A given frame is generated an increment of time after the preceding frame in the series of frames, with the increment of time depending on frame rate of the imager. The first and second series are generated synchronously with one another such that a frame in the first series has an associated frame in the second series that was captured at the same or similar time. The numbers of frames in the respective series can but need not be the same. For example, the second imaging modality may produce frames less frequently than the first imaging modality or vice versa.

At step 104, the first series of first imaging modality frames are displayed in combination with the first series of second imaging modality frames. The frames may be displayed in combination as overlay images, side-by-side, picture-in-picture, on separate displays, or in any other suitable manner. Display of the frames in combination can enable a practitioner to visualize different features of the tissue simultaneously. In embodiments in which the frames are displayed in real time as they are being generated during the surgical procedure, display of the combination of frames can assist the surgeon in performing the surgical procedure by enabling the surgeon to visualizes different features of interest. For example, in some embodiments, the displayed combination can include overlay images in which a fluorescence image is overlaid on a visible light image. The visible light image may enable the surgeon to visualize the surfaces of the tissue in the field of view and the fluorescence overlay may enable the surgeon to visualize a feature of interest that is beneath the surface of the tissue. This can help the surgeon locate the feature for performing a procedure on the feature or for aiding the surgeon in avoiding the feature, such as to avoid damaging the feature.

At step 106, a plurality of first imaging modality frames of the first series of first image modality frames and a plurality of second imaging modality frames of the first series of second imaging modality frames are stored in a memory. In some embodiments, all of the frames are stored, while in other embodiments only some of the frames are stored. Storage of fewer than all of the frames in the first and/or second series may reduce the amount of storage space required and/or the amount of processing required. In some embodiments only some of the frames of one imaging modality are stored while all of the frames of the other imaging modality are stored. This may be the case when, for example, the frame rates are different between the first and second imaging modalities.

Each first imaging modality frame may be stored in association with one of the second imaging modality frames based on when the frames were generated. First and second imaging modality frames generated at the same or similar time are stored in association with one another so that there is a link between the two frames indicating that they were generated at the same or similar time. The frames may be linked in the memory in any suitable manner, including by storing metadata, such as a time stamp or sequence identifier, with each frame or by storing the frames in a data structure or structures that preserves the association between the frames.

At step 108, a second series of first imaging modality frames generated by imaging the region of tissue of the subject according to the first imaging modality are received. The frames of the second series may be received from an imager as they are generated or may be received from a memory. The second series of first imaging modality frames may be generated immediately succeeding the first series of first imaging modality frames. In other words, there may be no interruption in frame generation by the imager between the last frame of the first series and the first frames of the second series. Frames generated according to the first imaging modality may be generated continuously according to the imaging frame rate. However, processing of the frames in the second series of first imaging modality frames may be different than processing of the frames in the first series of first imaging modality frames, as is explained further below.

In some embodiments, a second series of second imaging modality frames that corresponds to the second series of first imaging modality frames are also received. In other embodiments, second imaging modality frames are not generated as the second series of first imaging modality frames are generated, and therefore, there is no series of second imaging modality frames that was generated contemporaneously with the second series of first imaging modality frames. The second imaging modality frames may not be generated, for example, because imaging via the second imaging modality is paused for a period of time, such as to reduce exposure of the subject to radiation caused by the second imaging modality.

At step 110, the second series of first imaging modality frames are displayed in combination with one or more second imaging modality frames that are associated with the first series of second imaging modality frames stored in the memory. The combination of frames is displayed for visualizing features in the region of tissue of the subject that are captured by the first imaging modality and features in the region of tissue that are captured by the second imaging modality. According to various embodiments, the one or more second imaging modality frames displayed in this step are one or more of the second imaging modality frames of the first series of second imaging modality frames that were previously stored in the memory in step 106. According to various embodiments, the one or more second imaging modality frames are generated at least in part on one or more of the second imaging modality frames of the first series of second imaging modality frames that were previously stored in the memory. In some embodiments, the one or more second imaging modality frames are generated using a trained learning machine that processes at least a portion of the first series of first imaging modality frames, at least a portion of the first series of second imaging modality frames, and at least a portion of the second series of first imaging modality frames.

According to some embodiments, each frame in the second series of first imaging modality frames is combined with a second imaging modality frame stored in the memory for display or a second imaging modality frame generated using a trained learning machine. A second imaging modality frame may be used for display in combination with multiple frames of the second series of first imaging modality frames. For example, all of the frames of the second series of first imaging modality frames may be displayed in combination with the same second imaging modality frame, such as from the memory or generated using the learning machine. In other embodiments, each of the frames in the second series of first imaging modality frames is displayed with a different second imaging modality frame (stored in the memory or generated using the learning machine).

The second imaging modality frame or frames that are used to generate the display in step 110 depict a feature of the tissue as it was during a period prior to the period during which the second series of first imaging modality frames were generated. However, a given second imaging modality frame used for display in step 110 may depict the feature of the tissue in a state that is similar to the state of the feature (e.g., location and orientation within the field of view) at the time that the respective frame of the second series of first imaging modality frames was generated. Thus, combining the second imaging modality frame retrieved from the memory or a second imaging modality frame generated based on the first series of second imaging modality frames with a frame from the second series of first imaging modality frames may closely approximate the tissue in the state it is in when the frame from the second series of first imaging modality frames was generated.

Second imaging modality frames may be selected or generated for display in combination with frames in the second series of first imaging modality frames based on a similarity between a state of the tissue at the time that the second imaging modality frames were generated and a state of the tissue at the time that the frames in the second series of first imaging modality frames were generated. In some embodiments, the similarity between states of the tissue is captured by first imaging modality frames. Taking advantage of this, a second imaging modality frame can be selected or generated for display with a later generated first imaging modality frame based on a similarity between its associated first imaging modality frame stored in the memory and the later generated first imaging modality frame. In other words, the earlier generated second imaging modality frame or the generated second imaging modality frame should be sufficient for displaying with the later generated first imaging modality frame because the tissue is in the same or similar state, as reflected in the similarity between the first imaging modality frame generated at the time of the earlier generated second imaging modality frame and the later generated first imaging modality frame.

According to various embodiments, a similar first imaging modality frame is displayed in combination with a frame from the second series of first imaging modality frames and the similar first imaging modality frame is located using any suitable image similarity metric algorithm, such as a structural similarity metric algorithm or a mutual information metric algorithm. According to some embodiments, for each stored first imaging modality frame, a similarity metric is calculated with respect to the given frame in the second series of first imaging modality frames. In some embodiments, the first imaging modality frame with the highest similarity score is selected. In some embodiments, a first imaging modality frame is selected only if its similarity score is above a predefined threshold value.

According to some embodiments, for a given frame in the second series of first imaging modality frames, the memory is searched for a similar first imaging modality frame from the first series that has been stored in the memory. Upon locating a similar (or sufficiently similar) first imaging modality frame, its associated second imaging modality frame is retrieved from the memory and used in combination with the given frame in the second series of first imaging modality frames for display. Thus, a feature that was previously imaged using the second imaging modality but is no longer being imaged can continue to be displayed.

According to various embodiments, a second imaging modality frame is generated for display in combination with the frame from the second series of first imaging modality frames. According to various embodiments, the second imaging modality frame is generated using a trained machine learning algorithm that is fed at least a portion of the first series of first imaging modality frames, at least a portion of the first series of second imaging modality frames, and at least a portion of the second series of first imaging modality frames. The trained machine learning algorithm can be configured to generate a second imaging modality frame that corresponds with the at least a portion of the second series of first imaging modality frames such that the generated second imaging modality frame can be displayed in combination with display of at least one frame of the second series of first imaging modality frames to provide an indication to the user of what a second imaging modality would show if the second imaging modality were imaging the feature of interest. The generated second imaging modality frame(s) can be an artificial frame in the sense that it is not a frame captured by the second imaging modality system.

In some embodiments, a second imaging modality frame is generated by the trained machine learning algorithm for each frame in the second series of first imaging modality frames. In some embodiments, a generated second imaging modality frame is used for multiple frames in the second series of first imaging modality frames.

According to various embodiments, the learning machine was trained on training data that includes sets of first imaging modality frames and corresponding sets of second imaging modality frames. The training data includes respective imaging modality frames from different subjects and from the same and/or different procedures and can include similar anatomy as the portion of the subject imaged during the medical procedure of method 100 and/or can include different anatomy. Generally and broadly speaking, the machine learning algorithm learns the relationships between the characteristics of frames of the first imaging modality and the characteristics of frames of the second imaging modality. Based on these learned relationships, the trained learning machine can output a generated second imaging modality frame that corresponds to the one or more frames of the second series of first imaging modality frames by feeding the one or more frames of the second series of first imaging modality frames along with at least a portion of the first series of first imaging modality frames and at least a portion of the first series of first imaging modality frames.

Method 100 can be performed using any two imaging modalities in which one of the imaging modalities is persistent while the other imaging modality is periodic or intermittent. Features that can be imaged by the non-persistent imaging modality can continue to be displayed during periods of time when the features are no longer being imaged by the non-persistent imaging modality utilizing similarities between images generated by the persistent imaging modality.

In some embodiments, method 100 can be modified by using a third imaging modality in addition to the first and second imaging modalities. The third imaging modality can be a persistent imaging modality, like the first, and can be used for display in combination with the second imaging modality, instead of the first imaging modality. However, the first imaging modality can be used for locating stored second imaging modality frames during periods when the second imaging modality is not imaging the feature of interest, as discussed above. In these embodiments, it may be preferable to display the second imaging modality frames in combination with the third imaging modality frames rather than the first imaging modality frames, but the first imaging modality frames may be more suitable for identifying similar frames than the third imaging modality. Accordingly, the first imaging modality frames can be used for identifying similar frames and the third imaging modality frames can be used for display with the second imaging modality frames.

According to some embodiments, the three-imaging modality method includes receiving a first series of third imaging modality frames in addition to the first and second imaging modality frames (e.g., at step 102 of method 100). The third imaging modality frames are displayed in combination with the second imaging modality frames (e.g., instead of the first imaging modality frames at step 104 of method 100). Like step 106 of method 100, a plurality of the first imaging modality frames are stored along with a plurality of the second imaging modality frames. The third imaging modality frames need not be stored since they are not used for locating similar frames. Next, a second series of the third imaging modality frames are received along with a second series of the first imaging modality frames (e.g., at step 108 of method 100). The first imaging modality frames are used to for similarity identification, as discussed above, and the corresponding stored second imaging modality frame are displayed in combination with the second series of third imaging modality frames. Thus, the first imaging modality is used for locating second imaging modality frames with similar fields of view relative to later generated frames and the third imaging modality is used for display in combination with the first imaging modality.

To illustrate a three-imaging modality method, according to some embodiments, the second imaging modality (i.e., the non-persistent imaging modality) can be fluorescence imaging and the third imaging modality (the imaging modality for display along with the second) can be white light imaging. Instead of using the white-light images for similar frame identification, narrow-band imaging can be used, and the first imaging modality can be narrow-band imaging. Narrow-band imaging can provide increased contrast of vasculature and may provide stronger similarity signals relative to white light imaging. While the narrow-band imaging may provide stronger similarity signals, a practitioner may prefer white light images over narrow band images for visualization of the surgical field. Therefore, the narrow-band images are used for similar frame identification and the white light images are used for display.

Figure 2:
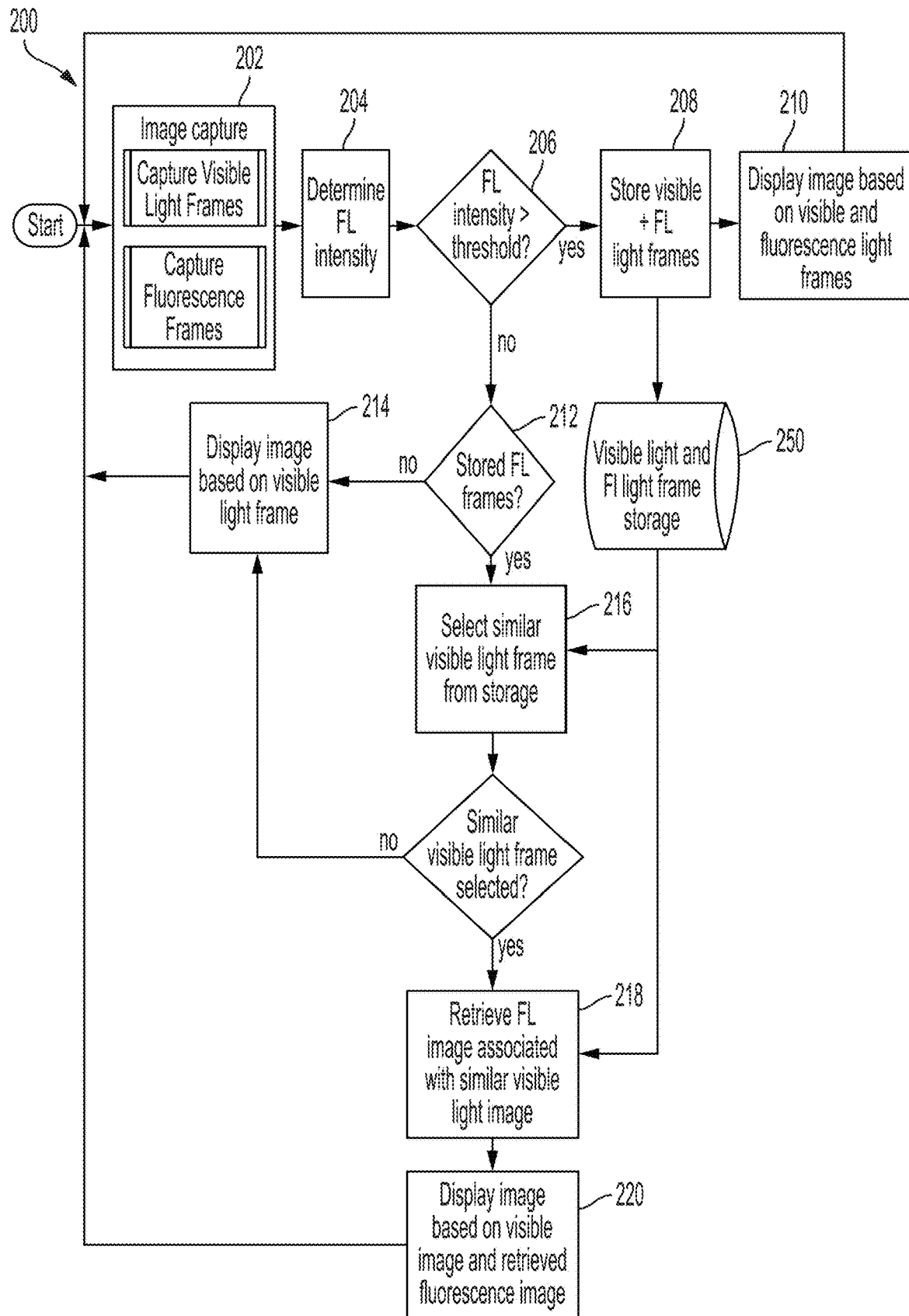
FIG. 2 illustrates a method for persistent visualization of tissue of a subject using a visible light imaging modality and a fluorescence imaging modality, according to some embodiments.

FIG. 2 illustrates a method 200 for persistent visualization of tissue of a subject using visible light and fluorescence imaging modalities, according to some embodiments. Method 200 can be used to persistently display a feature of interest of tissue through which a fluorescence imaging agent passes periodically during an imaging session.

At step 202, visible light and fluorescence light images of the tissue of the subject are captured. The tissue of the subject may be illuminated with visible light, such as white light, and visible light reflected from the tissue may be captured by an imager, which generates a visible image frame. The tissue may also be illuminated with fluorescence excitation light that causes the fluorescence imaging agent in at least a portion of the tissue to emit fluorescence radiation. The imager captures the fluorescence radiation from the portion of the tissue and generates a fluorescence image frame. The visible light frame and the florescence light frame may be generated simultaneously or may be generated sequentially.

At step 204, the fluorescence image frame is analyzed to determine a level of fluorescence intensity in the frame. The level of fluorescence intensity in the frame can indicate whether the imaging agent is within the field of view. The level of fluorescence intensity in the frame may be determined in any suitable manner. For example, the level of fluorescence intensity may be based on a peak fluorescence intensity in the frame, an average fluorescence intensity throughout the frame, or a percentage of the frame that is above a threshold intensity.

At step 206, the level of fluorescence intensity in the frame is compared to a predetermined threshold value to determine whether the level of intensity is above the threshold value. A level of intensity that is above the predetermined threshold can indicate that the imaging agent is present in the field of view or is present in an amount that can be useful for display. A level of intensity that is below the predetermined threshold can indicate that the imaging agent is not in the field of view, has reduced to a level that may no longer be useful for display, or has not yet increased to a level that is useful for display.

The threshold value can set be set based on how the level of intensity is determined. For example, for embodiments in which the level of fluorescence intensity is based on the maximum fluorescence intensity in the frame, the predetermined threshold can be set as an intensity value that is associated with imaging agent being within the field of view. As another example, for embodiments in which the level of fluorescence intensity is based on a percentage of the frame that is above a threshold intensity, the predetermined threshold value can be a percentage that is associated with the imaging agent being present in at least the percentage of the frame.

If the level of fluorescence intensity is determined to be above the predetermined threshold at step 206, then the fluorescence frame is stored in a reconstruction memory 250 along with the corresponding visible light frame at step 208. The two frames are stored in association with one another so that the relationship between the two in terms of being captured at the same or similar time is retained. For example, one or both of the frames can be stored with metadata that identifies the corresponding other frame. In embodiments in which the visible light frame and the fluorescence light frame are captured simultaneously (or very close in time), then the visible light frame captured at the same time as the fluorescence light frame is stored in association with the fluorescence light frame. In embodiments in which the frames are captured sequentially, then the visible light frame captured either before or after the fluorescence light frame can be stored in association with the fluorescence light frame. Whether the preceding or succeeding visible light frame is stored with the fluorescence light frame can depend on, for example, the relative periods of time between frame captures.

Figure 3:
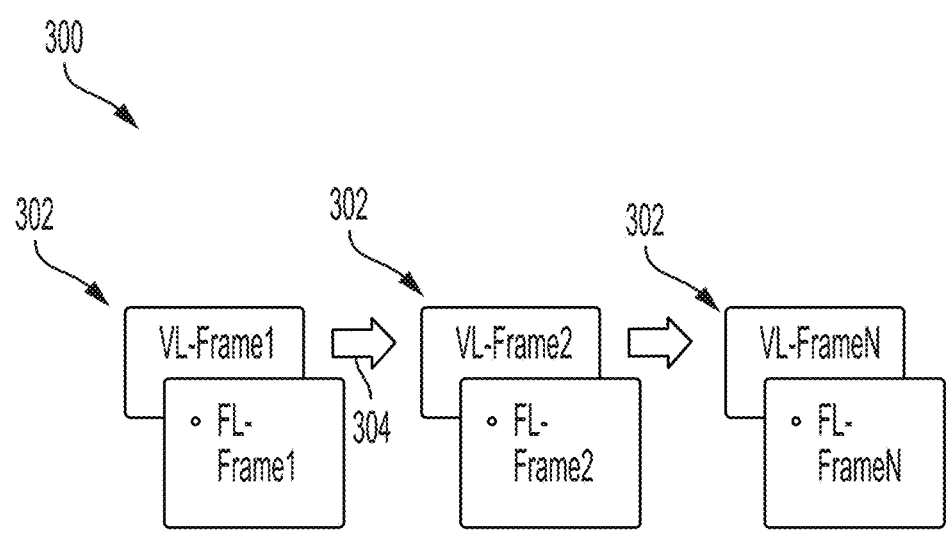
FIG. 3 illustrates an example of a reconstruction memory storing previously captured imaging frames.

FIG. 3 illustrates an example of a reconstruction memory, such as reconstruction memory 250, for storing visible and fluorescence light frames. Reconstruction memory 300 includes n sets 302 of visible light and fluorescence frames that are stored in association with one another. Visible light frame 1 is stored in association with fluorescence light frame 1 indicating that the two frames were captured at the same or similar time. Visible light frame 2 is associated with fluorescence light frame 2, which was capture at the same or similar time. This storage scheme is repeated for each of n sets of visible light and fluorescence frames. According to some embodiments, sets of frames may be stored along with an indication of when they were generated, as represented by arrows 304. For example, the frames may be stored so that it can be determined that frame set 1 was generated prior to frame set 2, and so on. This may be done using metadata associated with each image frame file, such as a time stamp, or through any other suitable method. In some embodiments, each frame generated during a given period is to be stored. However, in other embodiments, only a portion of the frames generated during a given period may be stored. For example, frames may be stored at a rate that is a fraction of the frame rate, which can help reduce the amount of storage space and can decrease the amount of processing needed to search the stored frames.

Returning to FIG. 2, at step 210, the visible light frame and the fluorescence light frame are displayed on a display. The frames can be combined into, for example, an overlay, a false color image, or any other suitable combination image and displayed on the display. The frames can be displayed side-by-side on a single display or on separate displays. In some embodiments, the image frames are stored in a video capture device for future display and/or analysis. The order of steps 208 and 210 can be reversed or the steps can be performed in parallel. The method may then return to step 202 for generation of the next visible light frame and fluorescence light frame.

If the level of fluorescence intensity is determined to be below the predetermined threshold at step 206, which can indicate that the imaging agent is not present in the field of view or not present to a sufficient degree, then the fluorescence frame is not saved in the storage 250 and a determination is made at step 212 whether there are stored fluorescence light frames in the reconstruction memory 250. If there are no stored fluorescence light frames, which may be the case, for example, in the beginning stages of an imaging session when the imaging agent has yet to reach the field of view for the first time, then the visible light image alone may be displayed and/or stored for future viewing and/or processing at step 214. The method then returns to step 202 for generation of the next visible light frame and fluorescence light frame.

If a determination is made at step 212 that there are stored fluorescence light frames in the reconstruction memory 250, then at step 216, the visible light frames in the reconstruction memory are searched for a stored visible light frame that is similar to the visible light frame captured at step 202. This may be done using any suitable image similarity metric algorithm, such as a structural similarity metric algorithm or a mutual information metric algorithm. According to some embodiments, for each stored visible light frame, a similarity metric is calculated with respect to the newly acquired visible light image.

In some embodiments, the visible light frame with the highest similarity score is selected. The frame with the highest similarity score should more closely resemble the newly acquired visible light image relative to frames with lower similarity scores. In some embodiments, a frame is selected only if the similarity score is above a predefined threshold value. The threshold value may be selected such that frames that are not similar enough are not selected. For example, according to various embodiments, a frame may only be selected if its similarity score is at or above 0.80, 0.85, 0.90, 0.95, 0.98, or any other suitable threshold value.

Figure 4:
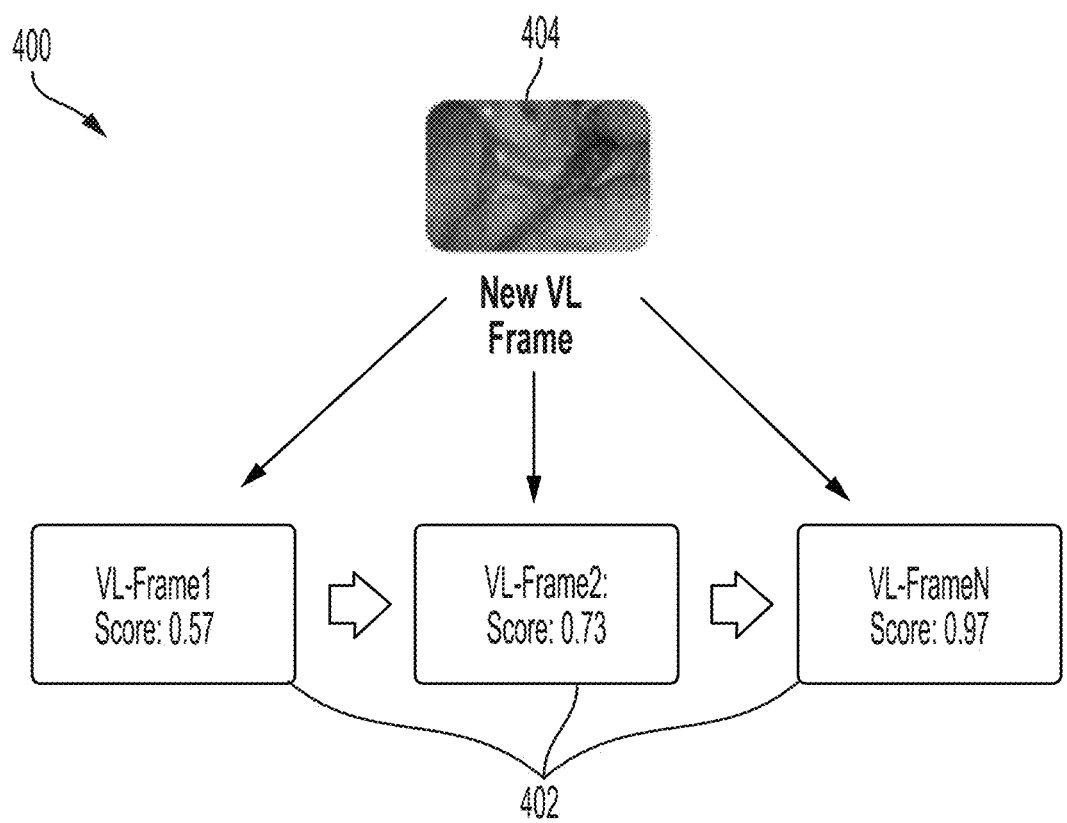
FIG. 4 illustrates the identification of a visible light frame stored in reconstruction memory that is similar to a newly acquired visible light frame, according to some embodiments.

FIG. 4 illustrates the selection of a visible light frame from the reconstruction memory, according to some embodiments. The reconstruction memory 400 includes n visible light frames. A similarity metric 402 is calculated for each visible light frame relative to the newly acquired visible light frame 404. As illustrated, the $n^{th}$ visible light frame has the highest similarity score—0.97. According to various embodiments, this visible light frame may be selected if the similarity score of 0.97 is above the predetermined threshold—e.g., a threshold of 0.95—as discussed above.

Returning to FIG. 2, at step 218, if a similar visible light frame has been selected in step 216, then the fluorescence frame that is stored in the reconstruction memory 250 in association with the selected visible light frame selected in step 216 is retrieved from the reconstruction memory 250. A similar visible light frame can indicate that the tissue in the field of view is in a similar state and/or location as it was when the selected stored visible light frame was generated. Since the fluorescence light frame was captured at the same or approximately the same time as the selected stored visible light frame, then the fluorescence light frame should show the portion of tissue represented in the stored fluorescence light frame in the same state as it was in when the current visible light frame was captured. The lack of suitable fluorescence signature in the current fluorescence image, as determined in step 206 may be due to the imaging agent having passed through the field of view, not due to the portion of tissue having passed out of the field of view. Thus, by locating in memory a visible light frame that is similar to the newly acquired visible light frame, the fluorescence light frame stored in association with the located visible light frame should represent the tissue as it was when the newly acquired visible light image was generated.

Once the stored fluorescence image has been retrieved from the reconstruction memory 250 at step 218, the newly acquired visible light frame and the retrieved stored fluorescence frame may be used to generate an image that can be displayed and/or stored for future viewing and/or processing. As in step 210, the frames can be combined into, for example, an overlay, a false color image, or any other suitable combined image or combination of images and displayed on the display. In some embodiments, the frames can be displayed side-by-side on a single display or on separate displays. In some embodiments, the frames are stored in an image capture device for future display and/or analysis. The method may then return to step 202 for generation of the next visible light frame and fluorescence light frame.

Figure 5:
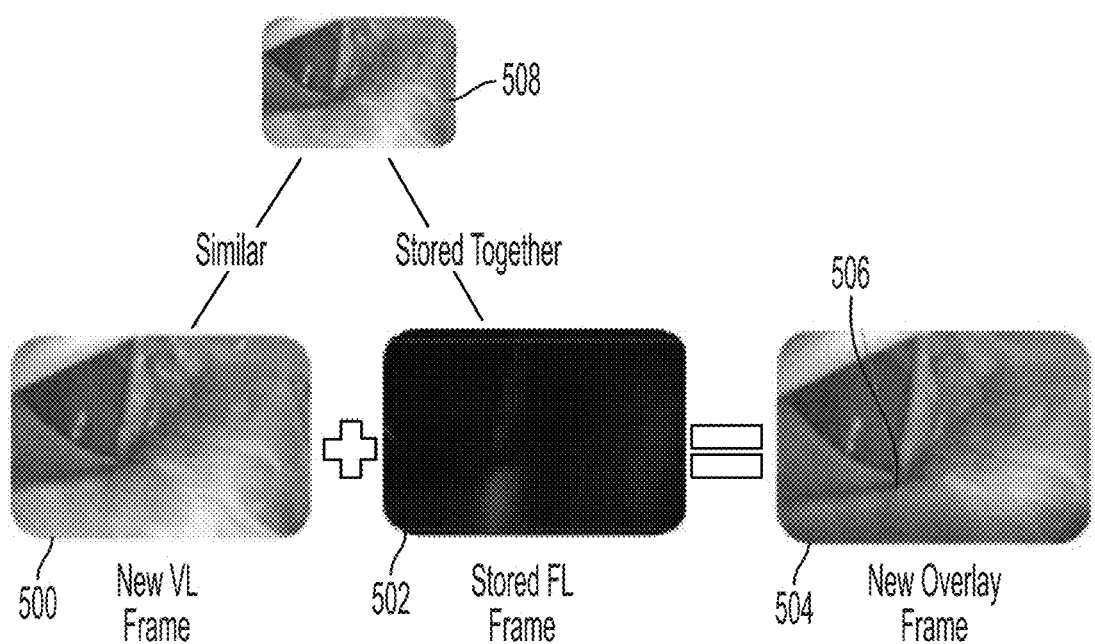
FIG. 5 illustrates combining a newly acquired visible light frame with a stored fluorescence light frame for persistent visualization of a feature of tissue of a subject, according to some embodiments.

FIG. 5 illustrates steps 216 through 220, according to some embodiments. The newly acquired visible light frame 500 is combined with a stored fluorescence light frame 502 to produce a new overlay frame 504. The stored fluorescence light frame 502 was selected for combining with the newly acquired visible light frame 500 by finding a stored visible light frame 508 that is similar to the newly acquired visible light frame 500 and retrieving its associated fluorescence light frame 502, according to the process described above. The new overlay frame 504 includes a representation of a fluorescing area 506 in the lower middle portion. This represents imaging agent that was present in the imaged tissue at the time that the stored fluorescence light frame 502 was generated but that has since disappeared from the field of view or reduced to a level that is no longer useful for display. Thus, the portion of the tissue that can be imaged using the imaging agent can continue to be represented in a displayed overlay image after the imaging agent has left the portion of the tissue.

According to some embodiments, if a similar visible light frame has not been selected at step 216, for instance, because the highest similarity score is not above the predetermined threshold, then the method proceeds to step 214 and the visible light frame alone may be displayed and/or stored for future viewing and/or processing. The method then returns to step 202 for generation of the next visible light frame and fluorescence light frame.

Method 200 can continue throughout an imaging session. In accordance with an imaging session in which an imaging agent passes periodically through the field of view, method 200 will result in periods of display of currently captured visible light frames in combination with currently captured fluorescence light frames (e.g., overlays)—periods during which the imaging agent is in the field of view. These periods will alternate with periods of display of currently captured visible light frames in combination with previously captured and stored fluorescence light frames—periods during which the imaging agent is absent from the field of view. Through method 200, the portion of the tissue that is captured via fluorescence imaging can continue to be represented on the display when the imaging agent is no longer present in the tissue.

According to some embodiments, steps 202, 204, 206, 208, and 210 are performed repeatedly as fluorescence frames continue to capture fluorescence from the imaging agent. This results in first series of visible light and fluorescence frames being saved in the reconstruction memory 250. Once the fluorescence intensity drops below the predetermined threshold in step 206, indicating that the fluorescence imaging agent has left the imaged region of tissue, storage of the fluorescence light frames ceases and steps 202, 204, 206, 212, 216, 218, and 220 are performed repeatedly, resulting in a second series of visible light frames being displayed in combination with one or more of the fluorescence frames that are stored in the reconstruction memory 250. This can continue until the level of fluorescence intensity in a fluorescence image rises above the predetermined threshold, at which time a new series of visible light and fluorescence frames are displayed and saved in the reconstruction memory 250. Thus, the reconstruction memory 250 can be repeatedly updated over time to increase the likelihood that a stored frame can be found that is similar to a newly generated frame.

According to some embodiments, method 200 is performed during a minimally invasive procedure. The visible light and fluorescence frames may be generated by an endoscopic imaging system utilizing an endoscope inserted into the surgical field during the procedure. The imaging system provides visible light and fluorescence excitation light to the surgical field and receives reflected visible light and fluorescence emission light from the surgical field. The reflected visible light and fluorescence emission are received via the same endoscope, ensuring that the visible light and fluorescence frames share the same field of view. The reflected visible light and fluorescence emission are directed by the endoscope and any suitable optics to one or more imaging sensors of the imaging system for generation of the visible light and fluorescence frames.

In some embodiments, the minimally invasive procedure is a laparoscopic procedure and the feature of interest that is imaged by the fluorescence imaging system is a ureter. A florescence imaging agent that concentrates in the urine is administered to the subject and the passage of the imaging agent in the urine through the ureter is used to image the ureter. Method 200 can be used to persistently visualize the ureter despite the peristaltic nature of the movement of the urine (and, thus, the imaging agent) through the ureter. This can enable the surgeon to continuously visualize the ureter throughout the procedure, helping the surgeon to avoid the ureter. This can help reduce the risk of damaging the ureter, reducing the complications associated with laparoscopic procedures.

Figure 6:
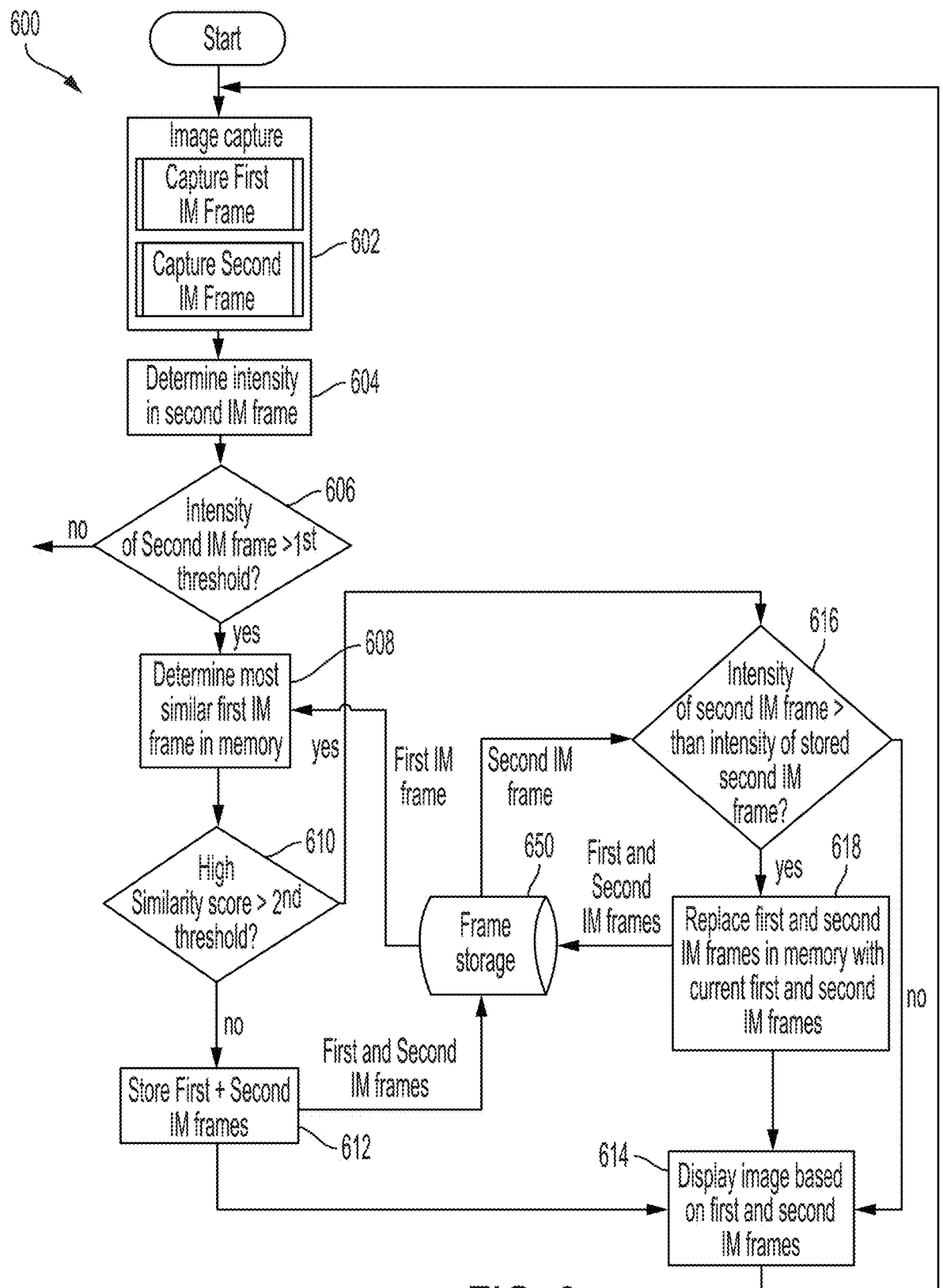
FIG. 6 illustrates a method for improving the efficiency of second imaging mode frame storage and retrieval, according to some embodiments.

FIG. 6 illustrates a method 600 for improving the efficiency of second imaging mode frame storage and retrieval, according to some embodiments. Method 600 can be used to reduce the number of frames that are stored in the memory, thereby decreasing the amount of storage space required and reducing the amount of searching that is done when selecting second imaging modality frames from the memory. Method 600 can be included as a part of any of the methods discussed above, such as method 100 and method 200.

At step 602, first and second imaging mode frames are captured (or received from an imager or memory). At step 604, a level of intensity in the second imaging mode frame is determined. This can be done in any suitable fashion, as discussed above, such as based on a maximum intensity in the frame, an average intensity in the frame, a proportion of the frame that is above a predetermined threshold, etc. At step 606, a determination is made whether the level of intensity determined at step 604 is above a first threshold. If not, then the method can continue in similar fashion to the "no" path at step 206 of method 200 of FIG. 2.

If the level of intensity is above the predetermined threshold at step 606, then the method continues to step 608 in which the most similar first imaging mode frame stored in the frame storage 650 is determined. This can be done by computing similarity metrics for each of the first imaging mode frames stored in the frame storage 650 relative to the first imaging mode frame captured (or received) at step 602. The stored first imaging mode frame having the highest similarity score is selected. At step 610, the similarity score of the selected first imaging mode frame is compared to a second predetermined threshold. If the similarity score is below the second threshold, indicating that the selected first imaging mode frame is not similar enough to the captured/received first imaging mode frame, then the method continues to step 612 in which the first and second imaging mode frames are stored in the frame storage 650 and then to step 614 in which an image that is based on the first and second imaging mode frames captured/received at step 602 is generated and displayed.

If, however, the similarity score determined at step 608 is determined to be above the second threshold at step 610, indicating that the selected first imaging mode frame is similar enough to the captured/received first imaging mode frame, then an intensity level of the second imaging mode frame that was captured/received at step 602 is compared to an intensity level of the stored second imaging mode frame that is associated with the selected first imaging mode frame at step 616. The intensity level for each of the frames can be determined in any suitable manner, such as using any of the methods discussed above with respect to the step 606. The intensity levels may be determined in the same manner as in step 606 or in a different manner.

If the level of intensity of the second imaging mode frame captured/received in step 602 is determined at step 616 to be greater than the intensity of the stored second imaging mode frame, then, at step 618, the stored first and second imaging mode frames are replaced in the frame storage 650 with the first and second imaging mode frames captured/received in step 602. Thus, for pairs of frames representing the same state of the imaged tissue within the field of view, the pair having the highest second imaging mode intensity is stored in the memory while the other pair is discarded. This can reduce the numbers of frames that are stored in the memory, thereby reducing the storage space required. Reducing the numbers of frames in memory can also reduce the amount of processing needed for identifying similar frames. Additionally, by storing the second imaging mode frames with the highest intensity, the display of features imaged by the second imaging mode can be enhanced.

The first and second imaging mode frames captured/received at step 602 are then displayed at step 614. The process then returns to step 602 for capturing/receiving the next first and second imaging mode frames.

Reference is made above to locating a stored first imaging modality frame that is similar to a later generated first imaging modality frame. In some embodiments, this process can include comparing entire frames to entire frames. In some embodiments, the process can additionally or alternatively include comparing sub-regions of frames. For example, in some embodiments, a similarity score can be generated based on corresponding sub-regions of frames (e.g., a center portion of each frame). This can reduce the computation cost and/or reduce the influence of regions of frames that are associated with low signal to noise ratio. In some embodiments, frames can be divided into sub-regions and similarity scores can be generated for each sub-region. Similarity scores for the sub-regions can be averaged to generate an average overall similarity score. In some embodiments, sub-regions can be assigned different weights and the overall similarity score can be a weighted average of the sub-scores.

In some embodiments, a registration step may be performed to align images with respect to one another. In some embodiments, the registration step is performed to ensure that the stored second imaging modality frame is displayed in the correct location and/or orientation with respect to the newly acquired first imaging modality frame. For example, upon locating a stored first imaging modality frame that is similar (e.g., meets the threshold requirement) to a newly acquired first imaging modality frame, a registration process may be performed to determine whether and to the extent that the stored frame should be translated and/or rotated to align to the newly acquired frame. Then, the translation and/or rotation information can be used to register the corresponding stored second imaging modality frame for display in combination with the newly acquired first imaging modality frame.

In some embodiments, a registration step is performed during the search for a similar stored first imaging modality frame. In some embodiments, a stored frame that has the highest similarity score for a newly acquired image but one that does not meet the threshold can be further analyzed to see if there is a sub-region of the frame that is similar enough (e.g., meets the similarity threshold) to a sub-region of the newly acquired image. The stored first imaging modality frame can be registered to the newly acquired first imaging modality frame and a similarity score can be generated for the respective overlapping regions of the frames. This overlapping region similarity score may be higher than the similarity score generated for the entire frame because it excludes non-corresponding portions of the frames. If the overlapping region similarity score is above the similarity threshold, then the corresponding region of the corresponding stored second imaging modality frame can be displayed in combination with the newly acquired first imaging modality frame with the correct location and orientation as determined by the registration process.

According to various embodiments, rather than selecting an earlier generated second imaging modality frame for display in combination with the second series of first imaging modality frames, one or more second imaging modality frames can be generated for display in combination with the second series of first imaging modality frames by using a trained machine learning algorithm. In contrast to method 200 in which an earlier generated second imaging modality frame is selected, an artificial second imaging modality frame can be generated by a trained machine learning algorithm that is fed at least a portion of the second series of first imaging modality frames. For example, a frame of the second series of first imaging modality frames can be fed to the trained machine learning algorithm and the algorithm can generate an artificial second imaging modality frame that corresponds to the frame fed to the learning machine. In some embodiments, the trained machine learning algorithm can additionally be fed portions of the first series of first and second imaging modality frames, which may improve the algorithm's performance in generating the artificial second imaging modality frame.

Figure 12:
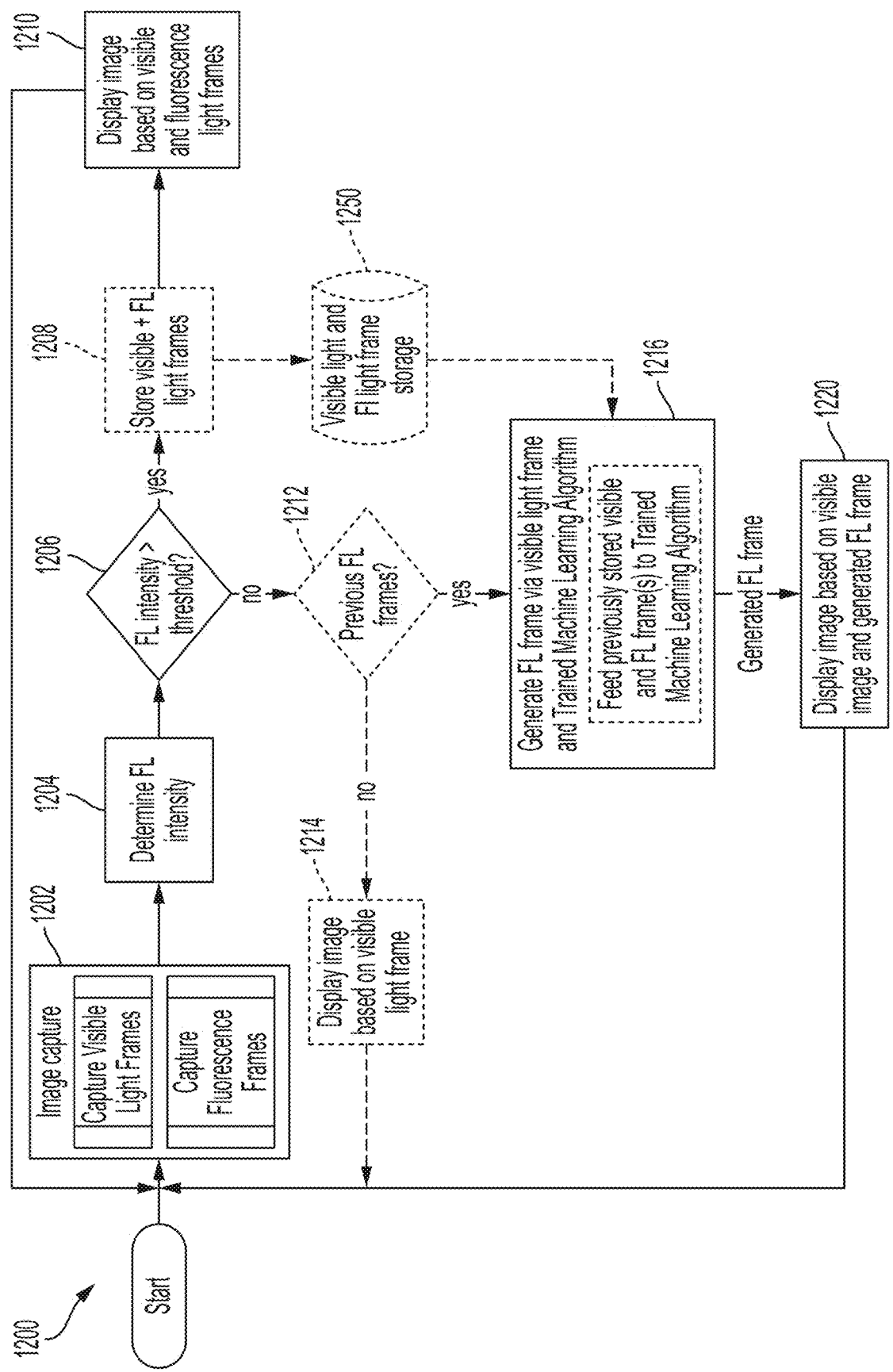
FIG. 12 illustrates a method for persistent visualization of tissue of a subject using a visible light imaging modality and a fluorescence imaging modality in which fluorescence frames are generated by a trained machine learning algorithm, according to some embodiments.

FIG. 12 illustrates a method 1200 for generating one or more second imaging modality frames using a trained learning machine and displaying the generated one or more second imaging modality frames with one or more frames of the second series of first imaging modality frames, according to various embodiments. The two imaging modalities used in the example of method 1200 illustrated in FIG. 12 are visible light and fluorescence imaging, but it is to be understood that method 1200 could be applied to any suitable imaging modalities. Method 1200 is similar to method 200 of FIG. 2 and similar steps are given similar labels and are not described in depth again here for brevity.

Similar to steps 202 to 210 of method 200 of FIG. 2, steps 1202 through 1210 include capturing visible light and fluorescence imaging frames, determining a level of fluorescence intensity in the fluorescence intensity frames, and storing and displaying the visible and fluorescence frames when it is determined at step 1206 that the fluorescence intensity is above a threshold. However, in method 1200, storing the visible and fluorescence frames at step 1208 is optional. Because the fluorescence frame that is displayed when the imaged fluorescence intensity drops below the threshold (as discussed further below) is an artificially generated frame and not a previously captured frame, there may be no need to store fluorescence frames at step 1208. However, in some embodiments, as discussed further below, previously captured and stored visible light and fluorescence frames can be used to improve the accuracy of the artificially generated fluorescence frame, and thus, step 1208 may be performed in order to store at least a portion of captured visible and fluorescence frames for feeding to the trained machine learning algorithm. In some embodiments, only a portion of previously captured visible and fluorescence light frames are stored in frame storage 1250. For example, in some embodiments, each newly captured frame overwrites a previously captured frame in step 1208 or only a certain limited number of previously captured frames are kept in storage 1250 (e.g., only the 5 previously captured frames are stored).

If the determination is made at step 1206 that the fluorescence intensity in a fluorescence frame is below the threshold, method 1200 may proceed to optional step 1212 in which a determination is made whether or not fluorescence images have been previously captured. If the determination is made that no fluorescence images have been previously captured, the method may proceed to optional step 1214 in which only the visible light frame is displayed. For example, at the beginning of the procedure before fluorescence dye has entered the field of view for the first time, the determination at optional step 1212 may be that no fluorescence frames have previously been captured (or at least none with a sufficiently high intensity) and, thus, only the visible light image is displayed. In some embodiments, optional step 1212 includes checking whether there are stored florescence frames. According to various embodiments, if the determination at step 1212 is that there are previously captured and/or stored fluorescence frames (e.g., of sufficiently high intensity), then method 1200 may proceed to step 1216. In some embodiments, step 1212 is omitted and the determination at step 1206 that the fluorescence intensity in the fluorescence frame is below the threshold leads directly to step 1216. At step 1216, a fluorescence frame is generated using a trained machine learning algorithm. According to various embodiments, the trained machine learning algorithm is provided with the current visible light frame captured at step 1202. Based on this input frame and the structure learned during its training, the machine learning algorithm can generate a fluorescence frame that approximates the current state of tissue as defined by the current visible light frame captured at step 1202. The artificially generated fluorescence frame can be displayed in combination with the visible light frame at step 1220.

In some embodiments, in addition to feeding the trained machine learning algorithm the current visible light frame, at least a portion of visible light and fluorescence frames stored in the reconstruction memory 1250 can be fed to the trained machine learning algorithm, which can provide temporal information to the algorithm that may improve the algorithm's performance in generating the artificial fluorescence frame. In some embodiments, the visible and fluorescence frames captured just before the fluorescence intensity dropped below the threshold (i.e., the most recent pair of visible and fluorescence frames in which the fluorescence intensity was sufficiently high) may be provided to the trained machine learning algorithm.

According to various embodiments, the machine learning algorithm was trained on pairs of visible and fluorescence frames previously captured during imaging sessions on other subjects during the same and/or different procedures. The machine learning algorithm learns the relationships between the characteristics of the visible light frames and the characteristics of their matched fluorescence light frames. Based on these learned relationships, the trained machine learning algorithm can generate an artificial fluorescence frame that corresponds to the visible light frame captured at step 1202.

According to various embodiments, the machine learning algorithm is a deep learning algorithm. In some embodiments, the deep learning algorithm is based on a conditional Generative Adversarial Network (GAN).

According to various embodiments, the trained machine learning algorithm is fed only the current visible light frame. In some embodiments, the algorithm is fed previously captured visible and fluorescence frames stored in reconstruction memory 1250. In some embodiments, all of the visible light and fluorescence frames stored in the reconstruction memory 1250 in addition to the current visible light frame are fed to the algorithm. In some embodiments, the trained machine learning algorithm is fed with a single pair of visible and fluorescence frames stored in the reconstruction memory 1250 or with an aggregate of multiple visible frames and an aggregate of multiple fluorescence frames stored in the memory.

According to various embodiments, an artificial fluorescence frame can be generated for each visible light frame captured during the period(s) in which the captured fluorescence frame intensity is below the threshold. In some embodiments, a single generated fluorescence frame is used for displaying in combination with several visible light frames. For example, a fluorescence frame may be generated only once and used for display with all of the visible light frames in a series or a fluorescence frame may be generated for every other visible light frame, every few visible light frames, or at any rate up to and including for each visible light frame in the series.

According to various embodiments, the artificial fluorescence frame generated by the trained learning machine can be enhanced using any suitable image enhancement technique or combination of techniques for improving the quality of the artificial fluorescence frame.

According to some embodiments, displaying an image based on a combination of a second imaging modality frame previously generated and stored in memory and a first imaging modality frame can include adjusting one or more aspects of the second imaging modality frame according to a level of uncertainty in how closely the second imaging modality frame reflects the current state of the tissue. The level of uncertainty can be based on a level of dissimilarity between the first imaging modality frame and the previously generated first imaging modality frame that is associated with the second imaging modality frame. This can be done in any of the methods describes above, including method 100, method 200, and/or method 1200. Performing this adjustment can minimize the chances that a feature that can be imaged by the second imaging modality is displayed incorrectly during periods when the feature is no longer being imaged using the second imaging modality, such as during step 110 of method 100 or during step 220 of method 200.

Figure 7:
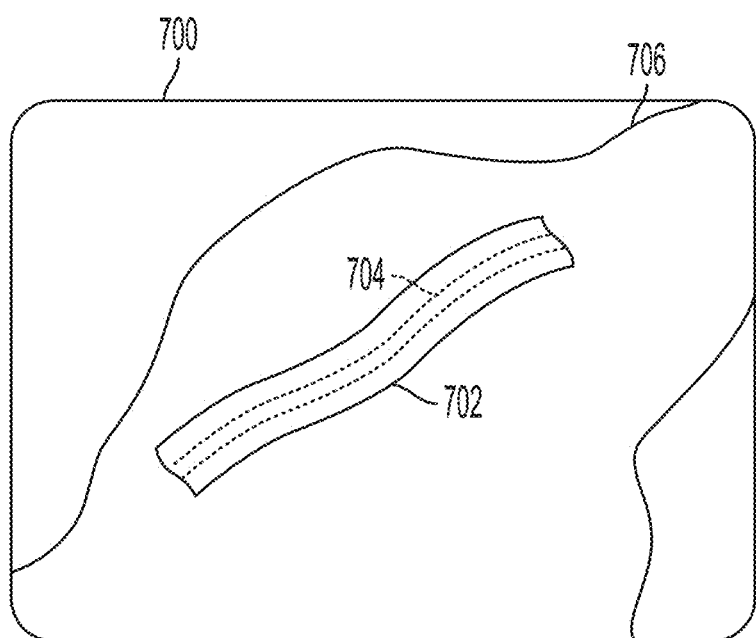
FIG. 7 illustrates an exemplary image of tissue of a subject in which a level of uncertainty in the accuracy of the appearance of a feature in the image is visually represented, according to some embodiments.

FIG. 7 illustrates an image 700 in which a level of uncertainty in the accuracy of a selected stored second imaging modality frame is visually represented. Image 700 is an overlay of a second imaging modality frame on a first imaging modality frame. The second imaging modality frame used to generate the overlay image 700 was generated at some time prior to the first imaging modality frame, saved in memory, and then retrieved from memory in accordance with the methods discussed above. The overlay image 700 includes a representation 702 of a feature that was imaged by the second imaging modality frame overlaid on top of tissue 706 imaged by the first imaging modality frame. However, the representation 702 is expanded relative to what was imaged by the second imaging modality frame stored in the memory. FIG. 7 includes an illustration of the representation 704 in the second imaging modality and, therefore, what the overlay image 700 would look like had the second imaging modality frame been used for the overlay without modification.

The difference in size—representation 702 compared to representation 704—can be based on an amount of dissimilarity between the first imaging modality frame used for the overlay 700 and the first imaging modality frame that is associated with the second imaging modality frame used for the overlay 700. As stated above, a second imaging modality frame stored in memory can be selected by computing similarity scores for each of the first imaging modality frames in the memory relative to a currently received first imaging modality frame. The first imaging modality frame in memory that has the highest similarity score may be identified and its associated second imaging modality frame selected for display with the currently received first imaging modality frame. The difference between the similarity score for the identified first imaging modality frame and a perfect score (which would indicate the same image) can be used to adjust the size of the representation 702 in the overlay 700 relative to the representation 704 in the selected second imaging modality frame. For example, for a similarity score of 0.95 on a scale of 0 to 1, the representation of the feature can be adjusted by 5% or some multiple of 5%, and for a similarity score of 0.98 on a scale of 0 to 1, the representation of the feature can be adjusted by 2% or some multiple of 2%.

Increases in size of a representation of a feature according to a level of uncertainty can be thought of as a confidence interval. The bounds of the expanded representation can represent the area in the field of view in which the feature is likely to be with a certain level of confidence. The greater the amount of expansion, the greater the confidence.

The level of uncertainty, in accordance with the principles discussed above, can be represented in any suitable manner. In some embodiments, a color of the representation of the feature in the combined image (e.g., overlay) is adjusted according to the level of uncertainty. For example, a low level of uncertainty—e.g., a relatively high similarity score—may be visually represented by displaying the feature imaged by the second imaging modality with the color green whereas a high level of uncertainty—e.g., a relatively low similarity score—may be visually represented by displaying the feature with the color red. Another example of a visual representation of a level of uncertainty is a numerical display of a level of uncertainty in the combined image. In some embodiments, a level of intensity of the representation of the feature in the combined image is modified based on the level of uncertainty, with lower levels of uncertainty being represented by higher levels of intensity and higher levels of uncertainty being represented by lower levels of intensity. In other words, a feature will be displayed brighter when the level of uncertainty is low and will be displayed more dimly when the level of uncertainty is high.

Embodiments have often been described above with respect to a periodic imaging modality—one in which the signal appears, disappears, and reappears. However, in some embodiments, the method may include persistent visualization based on an imaging modality in which the signal appears, disappears, and does not re-appear. For example, imaging agent may pass through a region of tissue just once, rather than periodically. Frames of the imaging agent moving through the tissue may be stored and used for persistent visualization, in accordance with the principles discussed above, without any further imaging agent moving through the region.

System for Persistent Visualization of a Feature of Interest

A system for persistent visualization of a feature of interest of tissue, according to some variations, includes an imaging system for acquiring one or more time series of images of tissue (e.g., one or more time series of visible light images, one or more time series of fluorescence images, one or more time series of x-ray images, one or more time series of ultrasonic images, etc.), and one or more processors and memory having instructions stored thereon, wherein the instructions when executed by the one or more processors cause the system to perform the methods substantially as described above for characterizing tissue and/or predicting the clinical data.

Figure 8:
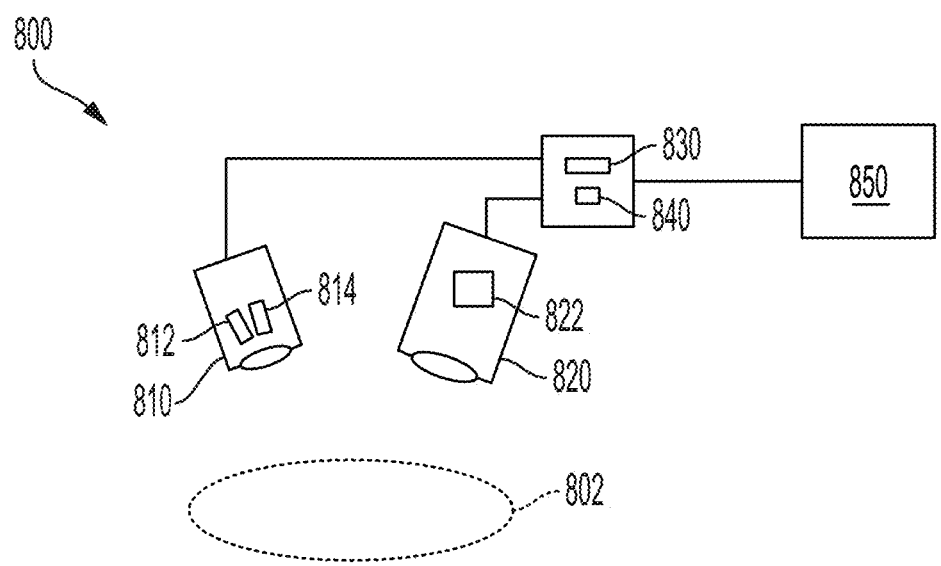
FIG. 8 is an illustrative depiction of an exemplary imaging system for persistent visualization of a feature of interest, according to some embodiments.

As illustrated in FIG. 8, various embodiments of an imaging system 800 for persistent visualization of a feature of interest of tissue 802 (e.g., a tissue region of interest) may include: an image acquisition assembly 820 with at least one image sensor 822 configured to acquire a sequence of video frames depicting the tissue and/or one or more features of the tissue; and a processor 830.

Figure 9:
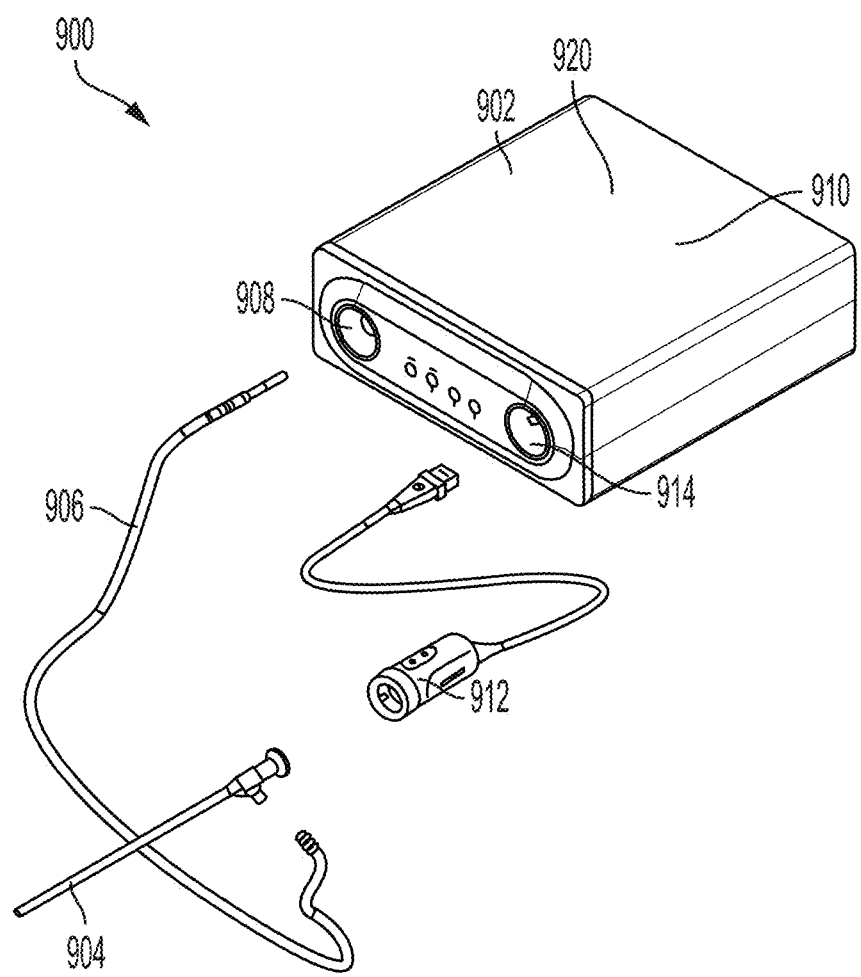
FIG. 9 illustrates an endoscopic imaging system, according to some embodiments.

In some variations, at least part of the imaging system may be embodied in an endoscopic imaging system, such as for minimally-invasive procedures. For example, as shown in FIG. 9, an endoscopic imaging system 900 may include an illuminator 902 with a light source assembly configured to provide visible light and/or fluorescence excitation light to a surgical laparoscope 904 via a light guide 906 that is connected to the illuminator 902 via a light guide port 908. A processor 910 and/or controller 920 may, in some variations, be within the same housing as the illuminator 902, as shown in FIG. 9, and may be configured to perform at least some of the aspects of any of the methods described herein, including method 100 and method 200 described above. An image acquisition assembly 912 may receive signals via connection to the laparoscope 904, and may pass acquired images to the processor 910 via connection to the processor 910 such as through port 914. Certain aspects of the light source assembly, image acquisition assembly, processor, and/or controller may be similar to those described in more detail below.

Light Source Assembly

As shown in the schematic of FIG. 8, the imaging system 800 may include a light source assembly 810 including a visible light source 812 that emits visible light (e.g., full spectrum visible light, narrow band visible light, or other portions of the visible light spectrum) and/or an excitation light source 814 that emits excitation light for exciting fluorophores in the tissue 802 and causing fluorescence emission.

The visible light source 812 is configured to emit visible light for illumination of the object to be imaged. In some variations, the visible light source may include one or more solid state emitters, such as LEDs and/or laser diodes. For example, the visible light source may include blue, green, and red (or other color components) LEDs or laser diodes that in combination generate white light illumination. These color component light sources may be centered around the same wavelengths around which the image acquisition assembly (described further below) is centered. For example, in variations in which the image acquisition assembly includes a single chip, single color image sensor having an RGB color filter array deposited on its pixels, the red, green, and blue light sources may be centered around the same wavelengths around which the RGB color filter array is centered. As another example, in variations in which the image acquisition assembly includes a three-chip, three-sensor (RGB) color camera system, the red, green, and blue light sources may be centered around the same wavelengths around which the red, green, and blue image sensors are centered.

The excitation light source 814 is configured to emit excitation light suitable for exciting intrinsic fluorophores and/or extrinsic fluorophores (e.g., a fluorescence imaging agent introduced into the object) located in the object being imaged. The excitation light source 814 may include, for example, one or more LEDs, laser diodes, arc lamps, and/or illuminating technologies of sufficient intensity and appropriate wavelength to excite the fluorophores located in the object being imaged. For example, the excitation light source may be configured to emit light in the near-infrared (NIR) waveband (such as, for example, approximately 805 nm light), though other excitation light wavelengths may be appropriate depending on the application.

Figure 10:
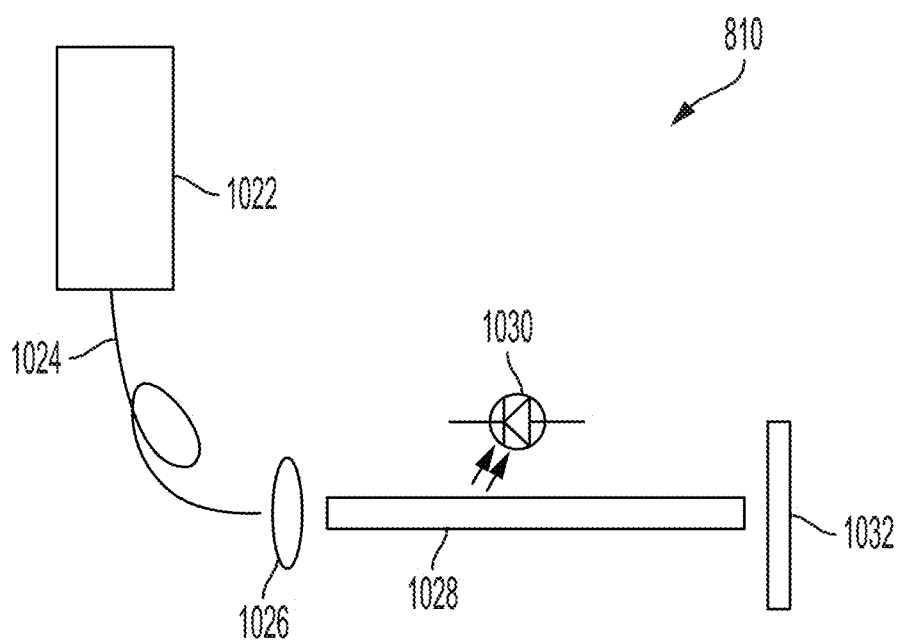
FIG. 10 is an illustrative depiction of an exemplary illumination module of an imaging system, according to some embodiments.

The light source assembly 810 may further include one or more optical elements that shape and/or guide the light output from the visible light source 812 and/or excitation light source 814. The optical components may include one or more lenses, mirrors (e.g., dichroic mirrors), light guides and/or diffractive elements, e.g., so as to help ensure a flat field over substantially the entire field of view of the image acquisition assembly 820. For example, as shown in the schematic of FIG. 10, the output 1024 from a laser diode 1022 (providing visible light or excitation light) may be passed through one or more focusing lenses 1026, and then through a light guide 1028. The light may be further passed through an optical diffractive element 1032 (e.g., one or more optical diffusers). Power to the laser diode 1022 may be provided by, for example, a high-current laser driver and may optionally be operated in a pulsed mode during the image acquisition process according to a timing scheme. An optical sensor such as a solid state photodiode 1030 may be incorporated into the light source assembly and may sample the illumination intensity produced by one or more of the light sources, via scattered or diffuse reflections from the various optical elements.

Image Acquisition Assembly

Figure 11:
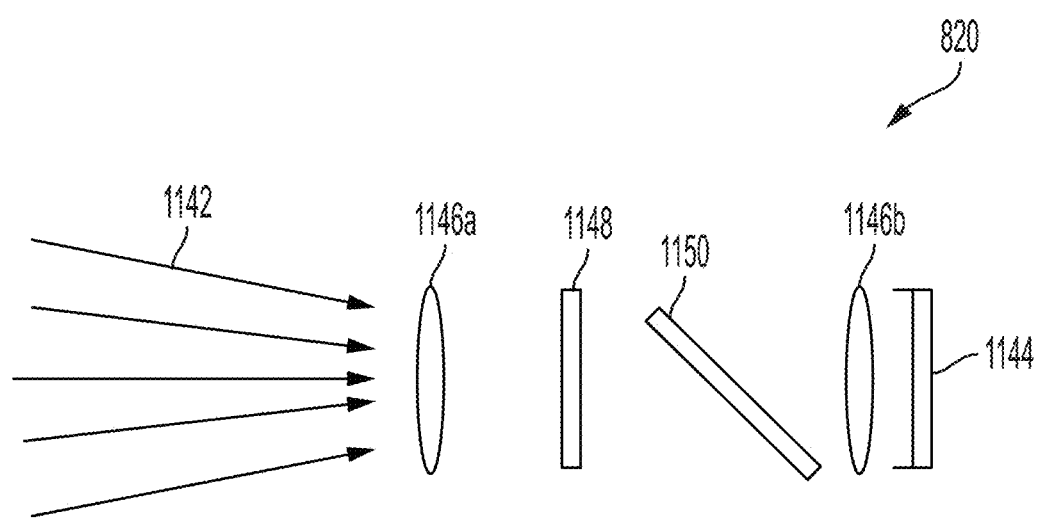
FIG. 11 is an exemplary camera module of an imaging system for imaging tissue of a subject, according to some embodiments.

The image acquisition assembly 820 may acquire reflected light video frames based on visible light that has reflected from the object, and/or fluorescence video frames based on fluorescence emitted by fluorophores in the object that are excited by the fluorescence excitation light. As shown in FIG. 11, the image acquisition assembly 820 may acquire images using a system of optics (e.g., one or more lenses 1146a, one or more filters 1148, one or more mirrors 1150, beam splitters, etc.) to collect and focus reflected light and/or fluorescent light 1142 onto an image sensor assembly 1144. The image sensor assembly 1144 may include at least one solid state image sensor. The one or more image sensors may include, for example, a charge coupled device (CCD), a CMOS sensor, a CID, or other suitable sensor technology. In one variation, the image sensor assembly 1144 may include a single chip, single image sensor (e.g., a grayscale image sensor or a color image sensor having an RGB color filter array deposited on its pixels). In another variation, the image acquisition assembly may include a three-chip, three-sensor (RGB) image sensor assembly 1144.

Processor and Controller

As shown in the schematic of FIG. 8, the system 800 may include a processor 830. The processor 830 may include, for example, a microprocessor or other suitable central processing unit. In particular, the processor 830 may be configured to execute instructions to perform aspects of the methods described herein. As visible light frames and/or fluorescence frames are acquired, at least a portion may be stored in a memory unit for record-keeping purposes and/or retrieval for analysis during other aspects of the method, as described below.

As shown in the schematic of FIG. 8, the system may include a controller 840, which may be embodied in, for example, a microprocessor and/or timing electronics. In some variations, a single image sensor may be used to acquire both visible light video frames and fluorescence frames, and the controller 840 may control a timing scheme for the visible light source and/or the excitation light source, and the image acquisition assembly. This timing scheme may enable separation of the image signal associated with the visible light signal and the image signal associated with the fluorescence signal. In particular, the timing scheme may involve illuminating the object with illumination light and/or excitation light according to a pulsing scheme, and processing the visible light image signal and fluorescence image signal with a processing scheme, wherein the processing scheme is synchronized and matched to the pulsing scheme (e.g., via a controller) to enable separation of the two image signals in a time-division multiplexed manner. Examples of such pulsing and image processing schemes have been described in U.S. Pat. No. 9,173,554, filed on Mar. 18, 2009 and titled "IMAGING SYSTEM FOR COMBINED FULL-COLOR REFLECTANCE AND NEAR-INFRARED IMAGING," the contents of which are incorporated in their entirety by this reference. However, other suitable pulsing and image processing schemes may be used to acquire reference video frames and low light video frames simultaneously, for example to acquire reflected light video frames and fluorescence video frames simultaneously. Furthermore, the controller may be configured to control the timing scheme for the visible light source and/or the excitation light source, and the image acquisition assembly based at least in part on the relative movement between the image acquisition assembly and the object.

Other Hardware

In some variations, the system may include image stabilizing technology that helps compensate for some ranges of motion (e.g., caused by unsteady hands holding the image acquisition assembly) in the acquired images. The image stabilizing technology may be implemented in hardware, such as with optical image stabilization technology that counteracts some relative movement between the image acquisition assembly and the object by varying the optical path to the image sensor (e.g., lens-based adjustments and/or sensor-based adjustments). Additionally, or alternatively, the image stabilization technology may be implemented in software, such as with digital image stabilization that counteracts some relative movement between the image acquisition assembly and the object (e.g., by shifting the electronic image between video frames, utilizing stabilization filters with pixel tracking, etc.). Such image stabilizing technology may, for example, help correct for motion blur in the characteristic low light video output (or in the acquired low light video frames) resulting from relative motion during long exposure periods.

The system may, in some variations, include one or more hardware motion sensors (e.g., gyroscope, accelerometer) that measure absolute motion of the image acquisition assembly. Information from these motion-measuring sensors may be used, in addition or as an alternative to the above-described motion-estimation algorithms, to determine which imaging mode of the system is suitable for a given set of circumstances.

Additionally, the system may include one or more data modules 850 that communicates and/or stores some or all of the acquired frames and/or information generated from the image data. For instance, the data module 850 may include a display (e.g., computer screen or other monitor), recorder or other data storage device, printer, and/or picture archiving and communication system (PACS). The system may additionally or alternatively include any suitable systems for communicating and/or storing images and image-related data.

A kit may include any part of the systems described herein, and/or the tangible non-transitory computer-readable medium described above having computer-executable (readable) program code embedded thereon that may provide instructions for causing one or more processors, when executing the instructions, to perform one or more of the methods described herein. For instance, the instructions may cause one or more processors, when executing the instructions, to perform method for persistent visualization of a feature of interest of tissue of a subject according to method 100, method 200, and/or any other method or combination of methods described herein. Furthermore, the kit may include instructions for use of at least some of its components (e.g., for installing the computer-executable (readable) program code with instructions embedded thereon, etc.).

In other variations, a kit may include any part of the systems described herein and a fluorescence agent such as, for example, a fluorescence dye such as methylene blue or any suitable fluorescence agent or a combination of fluorescence agents. In some variations, a suitable fluorescence agent is an agent which can accumulate in urine and which fluoresces when exposed to appropriate excitation light energy.

In general, the optical agent may be used in conjunction with a range of surgical methods. For example, the optical agent may be used in "open" procedures or in minimally invasive surgeries, sometimes referred to as bandaid or keyhole surgeries. In open procedures, an incision sufficiently large to expose the entire operative area is made with a scalpel or other knife. In minimally invasive surgeries, one or more much smaller incisions are typically made, through which a laparoscope and/or other endoscopic tools may be inserted to allow a surgeon to view and/or surgically manipulate a patient's organs and/or tissues.

Imaging Agents

According to various embodiments, imaging agents (also referred to as imaging dyes) that may be used for persistent visualization of ureters or other portions of the renal system are at least partially renally excretable. That is, upon administration to a patient, at least a fraction of the administered dose of the imaging agent will be excreted by way of the renal system. In general, the size and hydrophobicity of a pharmaceutical or diagnostic agent tends to influence the route by which it is excreted when it is administered to a patient. Small, hydrophilic molecules tend to be excreted via the renal system, whereas larger, hydrophobic molecules tend to be excreted via the hepatobiliary route. Thus, imaging agents according to some embodiments may preferably be relatively smaller in size and/or relatively more hydrophilic than dyes excreted predominantly via the hepatobiliary route. The imaging agents may be coupled or associated with moieties which render them more hydrophilic and thus increase their capacity to be excreted via the renal system.

Renally excretable imaging agents according to various embodiments may be chromophores or fluorophores, and the like. Optimal absorption or excitation maxima for the imaging agents may vary depending on the imaging agent employed, but in general, imaging agents according to various embodiments will absorb or be excited by light in the ultraviolet (UV), visible, or infrared (IR) range of the electromagnetic spectrum. For example, the non-ionizing radiation employed in the process of the present invention may range in wavelength from about 350 nm to about 1200 nm.

Methods for imaging the ureters can include injecting an imaging agent into the bloodstream, or direct cannulation, either anterograde or retrograde, into the ureters or bladder, such that it appears in the urine stream.

According to some embodiments, imaging agents for imaging portions of the renal system generally have a hydrodynamic diameter of less than 5 nm; are hydrophilic; and are not significantly positively charged. Agents that can be used include NIR fluorophores such as methylene blue, IR-786, CW800-CA, Cy5.5, Cy7, Cy7.5, IRdye™800CW (LICOR), and IRdye78 (LICOR).

The level of hydrophilicity of a compound plays a role in directing uptake to the kidney and/or liver; therefore, the hydrophilicity of a modifiable agent can be increased, e.g., by increasing the level of sulphonation, to increase uptake by liver and/or kidney. As described herein, agents that are unsulphonated, monosulphonated, or disulphonated are generally rapidly sequestered by the liver, but are not secreted into bile efficiently, and are thus not particularly useful to image the biliary tree. Agents that are trisulphonated, tetrasulphonated, pentasulphonated, or heptasulphonated are more likely to be secreted by the liver into bile, and are also more likely to be available in the circulation for filtration by the kidney into urine, and are thus useful for imaging the ureters and biliary tree. Agents that can be modified in this way include cyanine dyes such as Cy5.5 (Amersham Biosciences), e.g., by sulphonation.

Some agents are naturally taken up by the liver when injected systemically. To selectively label the ureters, such agents should be modified, e.g., by addition of a moiety such as a PEG i.e., by pegylation, that prevents uptake by the liver to improve their specificity for the ureters. Methods for pegylating compounds are known in the art.

Methylene Blue (MB)

As described herein, methylene blue (MB) has fluorescent properties. The emission wavelength (670 nm to 720 nm with a peak that shifts as a function of dye concentration) is within the NIR range at physiologically safe concentrations and therefore permits high sensitivity and high signal to background due to low autofluorescence in humans and animals. This characteristic allows MB to be used as a vascular contrast agent, using fluorescence imaging technology. Surprisingly, MB is secreted or partitions specifically into certain fluids and organs, including the thoracic duct, bile (allowing visualization of biliary tree), urine (allowing visualization of the ureters), heart myocardium, vasculature (allowing imaging of, inter alia, the myocardium, coronary artery, etc.), and pancreas (e.g., into beta cells, allowing visualization of that organ and tumors and metastases with a pancreatic origin, e.g., insulinomas).

Doses of 1.0-2.0 mg/kg of methylene blue are widely used clinically for the treatment of methemoglobinaemia, and much larger doses (on the order of 4.0-7.5 mg/kg) are administered for parathyroidal adenoma/hyperplasia detection. At the higher end, e.g., 7.5 mg/kg, MB administration sometimes causes severe adverse reactions, e.g., methemoglobinaemia or anaphylaxis. In addition, there are some reports indicating that intradermal injection of MB can cause skin damage. For example, the high doses used for sentinel node detection, e.g., around 4 ml of 30 mM MB, are associated with reports of injection site reactions. At these high concentrations, no fluorescence would be visible due to the concentration-dependent quenching of MB emissions. Thus, in general, the doses used in the methods described herein are about 10 times lower, and in some embodiments 100 times lower than those previously used, and are expected not to cause either skin damage or adverse reactions. For example, in some embodiments, the methods include the administration of a solution including at least 0.03% MB, e.g., about 0.03 to 10% MB, e.g., 0.05% to 10%, e.g., 1% to 3.5%. These percentages are weight/weight, i.e., a 10% solution is 100 mg/ml. In general, the total dose that will be used for most applications is about 1-4 mg/kg of body weight when administered systemically. So, for a 70 kg human, and a desired systemic dose of about 1 mg/kg, one would need 70 mg, which is equal to 7 ml of a 10%=100 mg/ml solution or 70 ml of a 1%=10 mg/ml solution. It is desirable to achieve a concentration in the tissue to be imaged of about 10-40 µM, e.g., about 20-30 µM. The concentration can vary depending on the local environment of the structure to be imaged, e.g., the pH of the environment, or the concentration of proteins. In some embodiments, an optimal concentration can be identified based, e.g., on the graphs in FIGS. 1A-D.

In summary, the MB fluorescence imaging methods described herein realize higher sensitivity with lower doses of MB. Methylene blue can be used as a lymphatic tracer, a bile duct and ureter indicator, and a vascular contrast agent. These broad indications introduce more options for intraoperative imaging. In addition, methylene blue can be used in combination with other fluorescent agents, such as ICG, to provide multi-wavelength, multi-color fluorescence imaging In some variations, a suitable fluorescence agent is an agent which can circulate with the blood (e.g., an agent which can circulate with, for example, a component of the blood such as plasma in the blood) and which fluoresces when exposed to appropriate excitation light energy. ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. In some embodiments, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement. According to some embodiments, the fluorescence imaging agent may be administered in various concentrations to achieve a desired circulating concentration in the blood. For example, in embodiments where the fluorescence imaging agent is ICG, it may be administered at a concentration of about 2.5 mg/mL to achieve a circulating concentration of about 5 µM to about 10 µM in blood. In various embodiments, the upper concentration limit for the administration of the fluorescence imaging agent is the concentration at which the fluorescence imaging agent becomes clinically toxic in circulating blood, and the lower concentration limit is the instrumental limit for acquiring the signal intensity data arising from the fluorescence imaging agent circulating with blood to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 µM to about 10 mM. Thus, in one aspect, the method comprises the step of administration of the imaging agent (e.g., a fluorescence imaging agent) to the subject and acquisition of the signal intensity data (e.g., video) prior to processing the signal intensity data according to the various embodiments. In another aspect, the method excludes any step of administering the imaging agent to the subject.

According to some embodiments, a suitable fluorescence imaging agent for use in fluorescence imaging applications to generate fluorescence image data is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). In various embodiments, the fluorescence imaging agent comprises a fluorescence dye, an analogue thereof, a derivative thereof, or a combination of these. An example of the fluorescence agent is a fluorescence dye, which includes any non-toxic fluorescence dye. In certain variations, the fluorescence dye may include a dye that emits light in the near-infrared spectrum. In certain embodiments, the fluorescence dye may include a tricarbocyanine dye such as, for example, indocyanine green (ICG). In other variations, the fluorescence dye may comprise methylene blue, ICG or a combination thereof. In certain embodiments the dye is or comprises fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy5.5, etc.), IRDye800CW, CLR 1502 combined with a targeting ligand, OTL38 combined with a targeting ligand, or a combination thereof, which is excitable using excitation light wavelengths appropriate to each imaging agent. In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations in which some or all of the fluorescence is derived from autofluorescence, one or more of the fluorophores giving rise to the autofluorescence may be an endogenous tissue fluorophore (e.g., collagen, elastin, NADH, etc.), 5-aminolevulinic acid (5-ALA), or a combination thereof.

In various embodiments, the fluorescence imaging agent may be provided as a lyophilized powder, solid, or liquid. In certain embodiments, the fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. In some embodiments, once the fluorescence imaging agent is reconstituted, it may be mixed with additional diluents and carriers. In some embodiments, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although a fluorescence imaging agent was described above in detail, other imaging agents may be used in connection with the systems, methods, and techniques described herein, depending on the medical imaging modality.

Surgical procedures in which processes according to various embodiments can be used to aid a surgeon include, but are not limited to, for example, total or partial hysterectomy, oophorectomy, tubal ligation, surgical removal of ovarian cysts, anterior repair of the vaginal wall, caesarean section, repair of a pelvic prolapse, pelvic mass resection, removal of a fallopian tube, adnexectomy (removal of a fallopian tube and an ovary), removal of an ectopic pregnancy, vasectomy, prostatectomy, hernia repair surgery, colectomy, cholecystectomy, appendectomy, hepatobiliary surgery (e.g., liver transplant surgery or removal of the gallbladder), splenectomy, distal or total pancreatectomy, the Whipple procedure, removal of inflammatory or malignant tumors in the abdominal or pelvic regions, abdominal or pelvic lymphadenectomy (removal of lymph nodes), and other surgical procedures performed in the abdominal or pelvic regions.

To various degrees, these and other surgical procedures performed in the abdomen or pelvic cavity carry a risk of accidental damage to the tissues of the renal system, and in particular, to the ureter. The risk of damage to the ureter and other tissues of the renal system is especially high in laparoscopic surgical procedures, because the surgeon has a limited view of the surgical area and is unable to use tactile perception to identify these structures. In one embodiment, therefore, one or more imaging agents, as discussed herein, are administered to avoid such accidental damage by permitting a surgeon to distinguish one or more tissues of the renal system from surrounding tissues. For example, processes according to various embodiments enable a surgeon to distinguish one or more tissues of the renal system from tissues of the male and female reproductive systems, tissues of the digestive tract, the pancreas, the gallbladder, the liver, the bile duct, and/or the spleen. Processes according to various embodiments also permit a surgeon to distinguish one or more tissues of the renal system from nearby arteries, veins, lymphatic vessels, and other tissues.

As previously noted, one or more imaging agents can be used to demarcate at least one tissue of the renal system of a patient during a surgical procedure. For example, various embodiments can be used to enable the surgeon or other healthcare individual to avoid the ureter(s), the bladder, and/or the urethra. In a healthy individual, urine flows from the kidneys through the ureter and collects in the bladder, where it is stored until it is eliminated from the body through the urethra. Thus, according to various embodiments, detection of the optical agent(s) in the ureter and bladder is possible due to the accumulation of the agent(s) in urine present in those structures. Detection of the optical agent(s) in the urethra is possible, for example, where residue of urine containing the optical agents is present on or within the walls of the urethra.

Alternatively, another aspect of the present invention is the use of one or more imaging agents to demarcate the target of a surgical procedure. Such surgical procedures include, but are not limited to, for example, nephrectomy, renal transplantation surgery, resection of a ureteral segment during removal of a tumor, bladder neck suspension surgery, and surgical removal of kidney stones.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method for visualizing tissue of a subject during a medical procedure, the method comprising:
   receiving, during the medical procedure, a first series of first imaging modality frames generated by imaging a region of tissue of the subject according to a first imaging modality, and a first series of second imaging modality frames generated by imaging the region of tissue of the subject according to a second imaging modality;
   displaying, during the medical procedure, the first series of first imaging modality frames in combination with the first series of second imaging modality frames for visualizing the region of tissue of the subject;
   storing, during the medical procedure, a plurality of first imaging modality frames of the first series of first image modality frames and a plurality of second imaging modality frames of the first series of second imaging modality frames in a memory;
   receiving, during the medical procedure, a second series of first imaging modality frames generated by imaging the region of tissue of the subject according to the first imaging modality; and
   displaying, during the medical procedure, the second series of first imaging modality frames in combination with one or more second imaging modality frames that are associated with the first series of second imaging modality frames for continuing to visualize the region of tissue of the subject.

2. The method of claim 1, further comprising selecting a frame of the plurality of second imaging modality frames stored in the memory for display in combination with a frame of the second series of first imaging modality frames based on a similarity between the frame of the second series of first imaging modality frames and a frame of the plurality of first imaging modality frames stored in the memory that is associated with the frame of the plurality of second imaging modality frames stored in the memory.

3. The method of claim 2, wherein selecting the frame of the plurality of second imaging modality frames comprises calculating a similarity score for the frame of the second series of first imaging modality frames and the frame of the plurality of first imaging modality frames stored in the memory.

4. The method of claim 3, wherein selecting the frame of the plurality of second imaging modality frames comprises determining that the similarity score is above a predetermined threshold.

5. The method of claim 3, wherein selecting the frame of the plurality of second imaging modality frames comprises determining that the similarity score is greater than similarity scores for other frame of the plurality of first imaging modality frames stored in the memory.

6. The method of claim 3, wherein an attribute of a display of the selected frame of the plurality of second imaging modality frames stored in the memory in combination with the frame of the second series of first imaging modality frames is based on the similarity score.

7. The method of claim 6, wherein the attribute comprises at least one of increasing an area of fluorescence and altering a color scheme based on the similarity score.

8. The method of claim 3, wherein the similarity score is a structural similarity metric, a mutual information metric, or a combination thereof.

9. The method of claim 1, wherein the second imaging modality is fluorescence imaging and the method further comprises ceasing to store second imaging modality frames in the memory based on a level of fluorescence intensity dropping below a threshold.

10. The method of claim 9, comprising, after ceasing to store second imaging modality frames in the memory, storing a second series of second imaging modality frames in the memory in response to an increase in a level of fluorescence intensity.

11. The method of claim 1, wherein the first series of second imaging modality frames comprises an image of a tissue feature that is not visible in the first series of first imaging modality frames.

12. The method of claim 1, wherein the first imaging modality comprises visible light imaging and second imaging modality comprises fluorescence imaging.

13. The method of claim 1, wherein the second imaging modality comprises fluorescence imaging and the method further comprises:
   receiving a third series of first imaging modality frames and a second series of second imaging modality frames; and
   storing a first frame of the third series of first imaging modality frames in place of a first frame of the first series of first imaging modality frames in the memory based on a level of fluorescence intensity of a first frame of the second series of second imaging modality frames that is associated with the first frame of the third series of first imaging modality frames.

14. The method of claim 13, further comprising storing the first frame of the second series of second imaging modality frames in place of a first frame of the first series of second imaging modality frames in the memory.

15. The method of claim 1, wherein the second imaging modality comprises imaging of an imaging agent and the method further comprises administering the imaging agent to the subject so that the imaging agent enters the region of tissue of the subject.

16. The method of claim 15, wherein the imaging agent is a fluorescence imaging agent and the tissue of the region of tissue of the subject comprises a ureter.

17. The method of claim 15, wherein the region of tissue of the subject comprises a ureter and the imaging agent is excretable in urine.

18. The method of claim 15, wherein the imaging agent comprises at least one of methylene blue, phenylxanthenes, phenothiazines, phenoselenazines, cyanines, indocyanines, squaraines, dipyrrolo pyrimidones, anthraquinones, tetracenes, quinolines, pyrazines, acridines, acridones, phenanthridines, azo dyes, rhodamines, phenoxazines, azulenes, azaazulenes, triphenyl methane dyes, indoles, benzoindoles, indocarbocyanines, benzoindocarbocyanines, derivatives having the general structure of 4,4-difluoro-4-bora-3a,4a-diaza-s-indacene, and conjugates thereof and derivatives thereof.

19. The method of claim 1, wherein the second imaging modality comprises imaging an imaging agent and at least a portion of the imaging agent is carried by urine transiting through a ureter.

20. The method of claim 1, comprising illuminating the region of tissue of the subject with visible light and fluorescence excitation light.

21. The method of claim 1, wherein the first series of first imaging modality frames and the first series of second imaging modality frames are generated using a single imaging sensor.

22. The method of claim 1, wherein the first series of first imaging modality frames and the first series of second imaging modality frames are generated using multiple imaging sensors.

23. The method of claim 1, wherein the first series of first imaging modality frames are white light frames.

24. The method of claim 1, wherein displaying the second series of first imaging modality frames in combination with one or more second imaging modality frames that are associated with the first series of second imaging modality frames comprises displaying an overlay image, side-by-side images, or a picture-in-picture image.

25. The method of claim 1, wherein the first series of first imaging modality frames is generated synchronously with the first series of second imaging modality frames.

26. The method of claim 25, wherein the first series of first imaging modality frames is generated simultaneously with the first series of second imaging modality frames.

27. The method of claim 1, wherein the medical procedure is a surgical procedure.

28. The method of claim 27, wherein the surgical procedure is an abdominal or pelvic surgical procedure.

29. The method of claim 28, wherein the abdominal or pelvic surgical procedure comprises at least one of total or partial hysterectomy, oophorectomy, tubal ligation, surgical removal of ovarian cysts, anterior repair of the vaginal wall, caesarean section, repair of a pelvic prolapse, pelvic mass resection, removal of a fallopian tube, adnexectomy, removal of an ectopic pregnancy, vasectomy, prostatectomy, hernia repair surgery, colectomy, cholecystectomy, appendectomy, hepatobiliary surgery, splenectomy, distal or total pancreatectomy, the Whipple procedure, and abdominal or pelvic lymphadenectomy.

30. The method of claim 1, wherein the first and second series of first imaging modality frames are displayed in real time.

31. The method of claim 1, wherein the first series of first imaging modality frames and the first series of second imaging modality frames are received from an imager.

32. The method of claim 1, wherein the first series of first imaging modality frames and the first series of second imaging modality frames are received from a memory.

33. The method of claim 1, further comprising generating the one or more second imaging modality frames that are associated with the first series of second imaging modality frames by processing at least a portion of the first series of first imaging modality frames by a trained learning machine.

34. The method of claim 33, wherein the trained learning machine was trained on imaging data not associated with the subject.

35. The method of claim 33, wherein the trained learning machine is based on a conditional Generative Adversarial Network.

36. A system for visualizing tissue of a subject during a medical procedure, the system comprising:
a display;
one or more processors;
memory; and
one or more programs, wherein the one or more programs are stored in the memory and configured to be executed by the one or more processors, the one or more programs including instructions for:
receiving, during the medical procedure, a first series of first imaging modality frames generated by imaging a region of tissue of the subject according to a first imaging modality, and a first series of second imaging modality frames generated by imaging the region of tissue of the subject according to a second imaging modality;
displaying, during the medical procedure, the first series of first imaging modality frames in combination with the first series of second imaging modality frames for visualizing the region of tissue of the subject on the display;
storing, during the medical procedure, a plurality of first imaging modality frames of the first series of first image modality frames and a plurality of second imaging modality frames of the first series of second imaging modality frames in the memory;
receiving, during the medical procedure, a second series of first imaging modality frames generated by imaging the region of tissue of the subject according to the first imaging modality; and
displaying, on the display and during the medical procedure, the second series of first imaging modality frames in combination with one or more second imaging modality frames that are associated with the first series of second imaging modality frames for continuing to visualize the region of tissue of the subject.

37. A non-transitory computer readable storage medium storing one or more programs for execution by one or more processors of a system for visualizing tissue of a subject during a medical procedure, the one or more programs comprising instructions for:
receiving, during the medical procedure, a first series of first imaging modality frames generated by imaging a region of tissue of the subject according to a first imaging modality, and a first series of second imaging modality frames generated by imaging the region of tissue of the subject according to a second imaging modality;
displaying, during the medical procedure, the first series of first imaging modality frames in combination with the first series of second imaging modality frames for visualizing the region of tissue of the subject;
storing, during the medical procedure, a plurality of first imaging modality frames of the first series of first image modality frames and a plurality of second imaging modality frames of the first series of second imaging modality frames in a memory;
receiving, during the medical procedure, a second series of first imaging modality frames generated by imaging the region of tissue of the subject according to the first imaging modality; and
displaying, during the medical procedure, the second series of first imaging modality frames in combination with one or more second imaging modality frames that are associated with the first series of second imaging modality frames for continuing to visualize the region of tissue of the subject.

\* \* \* \* \*